US011304729B2

(12) United States Patent
Pool et al.

(10) Patent No.: US 11,304,729 B2
(45) Date of Patent: *Apr. 19, 2022

(54) NON-INVASIVE ADJUSTABLE DISTRACTION SYSTEM

(71) Applicant: NuVasive Specialized Orthopedics, inc., San Diego, CA (US)

(72) Inventors: Scott Pool, Laguna Hills, CA (US); Blair Walker, Mission Viejo, CA (US)

(73) Assignee: NUVASIVE SPECIALIZED ORTHHOPEDICS, INC., San Diego, CA (US)

( * ) Notice: Subject to any disclaimer, the term of this patent is extended or adjusted under 35 U.S.C. 154(b) by 308 days.

This patent is subject to a terminal disclaimer.

(21) Appl. No.: 16/678,977

(22) Filed: Nov. 8, 2019

(65) Prior Publication Data

US 2020/0069339 A1    Mar. 5, 2020

Related U.S. Application Data

(63) Continuation of application No. 15/820,067, filed on Nov. 21, 2017, now Pat. No. 10,517,643, which is a
(Continued)

(51) Int. Cl.
*A61B 17/70* (2006.01)
*A61B 17/68* (2006.01)
*A61B 17/00* (2006.01)

(52) U.S. Cl.
CPC ........ *A61B 17/7004* (2013.01); *A61B 17/707* (2013.01); *A61B 17/7016* (2013.01);
(Continued)

(58) Field of Classification Search
CPC .......... A61B 17/025; A61B 2017/0256; A61B 17/7019; A61B 2017/681; A61B 2017/00411
See application file for complete search history.

(56) References Cited

U.S. PATENT DOCUMENTS 2,702,031 A    2/1955   Wenger
3,111,945 A   11/1963   Von Solbrig
(Continued)

FOREIGN PATENT DOCUMENTS

CA    2655093 A1    12/2007
CN    1697630 A     11/2005
(Continued)

OTHER PUBLICATIONS

International Preliminary Report on Patentability for PCT/US2010/023780, ISA, dated Aug. 23, 2011.
(Continued)

*Primary Examiner* — Samuel S Hanna
(74) *Attorney, Agent, or Firm* — Hoffman Warnick LLC

(57) ABSTRACT

A spinal distraction system includes a distraction rod having a first end and a second end, the first end being configured for affixation to a subject's spine at a first location, the distraction rod having a second end containing a recess having a threaded portion disposed therein. The system further includes an adjustable portion configured for affixation relative to the subject's spine at a second location remote from the first location, the adjustable portion comprising a housing containing a magnetic assembly, the magnetic assembly affixed at one end thereof to a lead screw, the lead screw operatively coupled to the threaded portion. A locking pin may secure the lead screw to the magnetic assembly. An O-ring gland disposed on the end of the housing may form a dynamic seal with the distraction rod.

19 Claims, 15 Drawing Sheets

Related U.S. Application Data continuation of application No. 14/332,286, filed on Jul. 15, 2014, now Pat. No. 9,848,914, which is a continuation of application No. 13/477,945, filed on May 22, 2012, now Pat. No. 8,974,463, which is a continuation of application No. 12/391,109, filed on Feb. 23, 2009, now Pat. No. 8,197,490.

(52) U.S. Cl.
CPC ....... *A61B 17/7019* (2013.01); *A61B 17/7011* (2013.01); *A61B 2017/00199* (2013.01); *A61B 2017/00212* (2013.01); *A61B 2017/00411* (2013.01); *A61B 2017/00876* (2013.01); *A61B 2017/681* (2013.01)

(56) References Cited

U.S. PATENT DOCUMENTS

| | | |
|---|---|---|
| 3,372,476 A | 3/1968 | Peiffer |
| 3,377,576 A | 4/1968 | Langberg |
| 3,397,928 A | 8/1968 | Galle |
| 3,512,901 A | 5/1970 | Law |
| 3,597,781 A | 8/1971 | Eibes |
| 3,810,259 A | 5/1974 | Summers |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,261,908 A | 11/1993 | Campbell, Jr. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,800,434 A | 9/1998 | Campbell, Jr. |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,283,156 B1 | 9/2001 | Motley |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,417,750 B1 | 7/2002 | Sohn |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |

(56) References Cited

U.S. PATENT DOCUMENTS

| | | |
|---|---|---|
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,765,330 B2 | 7/2004 | Baur |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,849,076 B2 | 2/2005 | Blunn et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,561,916 B2 | 7/2009 | Hunt et al. |
| 7,601,156 B2 | 10/2009 | Robinson |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,776,091 B2 | 8/2010 | Mastrorio et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,887,566 B2 | 2/2011 | Hynes |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,105,363 B2 | 1/2012 | Fielding et al. |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,517 B2 | 4/2012 | Trieu et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,211,179 B2 | 7/2012 | Molz, IV et al. |
| 8,216,275 B2 | 7/2012 | Fielding et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,298,240 B2 | 10/2012 | Giger et al. |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,419,801 B2 | 4/2013 | DiSilvestro et al. |
| 8,425,608 B2 | 4/2013 | Dewey et al. |
| 8,435,268 B2 | 5/2013 | Thompson et al. |
| 8,439,915 B2 | 5/2013 | Harrison et al. |
| 8,439,926 B2 | 5/2013 | Bojarski et al. |
| 8,444,693 B2 | 5/2013 | Reiley |

(56) References Cited

U.S. PATENT DOCUMENTS

| | | |
|---|---|---|
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,110 B2 | 7/2013 | Fielding et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |
| 8,709,090 B2 | 4/2014 | Makower et al. |
| 8,758,347 B2 | 6/2014 | Weiner et al. |
| 8,758,355 B2 | 6/2014 | Fisher et al. |
| 8,771,272 B2 | 7/2014 | LeCronier et al. |
| 8,777,947 B2 | 7/2014 | Zahrly et al. |
| 8,777,995 B2 | 7/2014 | McClintock et al. |
| 8,790,343 B2 | 7/2014 | McClellan et al. |
| 8,790,409 B2 | 7/2014 | Van den Heuvel et al. |
| 8,828,058 B2 | 9/2014 | Elsebaie et al. |
| 8,828,087 B2 | 9/2014 | Stone et al. |
| 8,840,651 B2 | 9/2014 | Reiley |
| 8,870,881 B2 | 10/2014 | Rezach et al. |
| 8,870,959 B2 | 10/2014 | Arnin |
| 8,894,663 B2 | 11/2014 | Giger et al. |
| 8,915,915 B2 | 12/2014 | Harrison et al. |
| 8,915,917 B2 | 12/2014 | Doherty et al. |
| 8,920,422 B2 | 12/2014 | Homeier et al. |
| 8,945,188 B2 | 2/2015 | Rezach et al. |
| 8,961,521 B2 | 2/2015 | Keefer et al. |
| 8,961,567 B2 | 2/2015 | Hunziker |
| 8,968,402 B2 | 3/2015 | Myers et al. |
| 8,992,527 B2 | 3/2015 | Guichet |
| 9,022,917 B2 | 5/2015 | Kasic et al. |
| 9,044,218 B2 | 6/2015 | Young |
| 9,060,810 B2 | 6/2015 | Kercher et al. |
| 9,078,703 B2 | 7/2015 | Arnin |
| 2002/0050112 A1 | 5/2002 | Koch et al. |
| 2002/0072758 A1 | 6/2002 | Reo et al. |
| 2002/0164905 A1 | 11/2002 | Bryant |
| 2003/0040671 A1 | 2/2003 | Somogyi et al. |
| 2003/0144669 A1 | 7/2003 | Robinson |
| 2003/0220643 A1 | 11/2003 | Ferree |
| 2003/0220644 A1 | 11/2003 | Thelen et al. |
| 2004/0011137 A1 | 1/2004 | Hnat et al. |
| 2004/0011365 A1 | 1/2004 | Govari et al. |
| 2004/0019353 A1 | 1/2004 | Freid et al. |
| 2004/0023623 A1 | 2/2004 | Stanch et al. |
| 2004/0055610 A1 | 3/2004 | Forsell |
| 2004/0133219 A1 | 7/2004 | Forsell |
| 2004/0138725 A1 | 7/2004 | Forsell |
| 2004/0193266 A1* | 9/2004 | Meyer ............... A61F 2/46 623/16.11 |
| 2005/0034705 A1 | 2/2005 | McClendon |
| 2005/0049617 A1 | 3/2005 | Chatlynne et al. |
| 2005/0055025 A1 | 3/2005 | Zacouto |
| 2005/0065529 A1 | 3/2005 | Liu et al. |
| 2005/0090823 A1 | 4/2005 | Bartimus |
| 2005/0159754 A1 | 7/2005 | Odrich |
| 2005/0234448 A1 | 10/2005 | McCarthy |
| 2005/0234462 A1 | 10/2005 | Hershberger |
| 2005/0246034 A1 | 11/2005 | Soubeiran |
| 2005/0251109 A1 | 11/2005 | Soubeiran |
| 2005/0261779 A1 | 11/2005 | Meyer |
| 2005/0272976 A1 | 12/2005 | Tanaka et al. |
| 2006/0004459 A1 | 1/2006 | Hazebrouck et al. |
| 2006/0009767 A1 | 1/2006 | Kiester |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047282 A1 | 3/2006 | Gordon |
| 2006/0052782 A1 | 3/2006 | Morgan et al. |
| 2006/0058792 A1 | 3/2006 | Hynes |
| 2006/0069447 A1 | 3/2006 | DiSilvestro et al. |
| 2006/0074448 A1 | 4/2006 | Harrison et al. |
| 2006/0079897 A1 | 4/2006 | Harrison et al. |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0213751 A1 | 9/2007 | Scirica |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0264605 A1 | 11/2007 | Belfor et al. |
| 2007/0265646 A1 | 11/2007 | McCoy |
| 2007/0270803 A1* | 11/2007 | Giger ............... A61B 17/8076 606/60 |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0048855 A1 | 2/2008 | Berger |
| 2008/0051784 A1 | 2/2008 | Gollogly |

(56) References Cited

U.S. PATENT DOCUMENTS

| | | |
|---|---|---|
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0172072 A1 | 7/2008 | Pool |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0062825 A1 | 3/2009 | Pool |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112207 A1 | 4/2009 | Walker et al. |
| 2009/0112262 A1 | 4/2009 | Pool |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0254088 A1 | 10/2009 | Soubeiran |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094302 A1 | 4/2010 | Pool |
| 2010/0094303 A1 | 4/2010 | Chang |
| 2010/0094304 A1 | 4/2010 | Pool |
| 2010/0094305 A1 | 4/2010 | Chang |
| 2010/0094306 A1 | 4/2010 | Chang et al. |
| 2010/0100185 A1 | 4/2010 | Trieu et al. |
| 2010/0106192 A1 | 4/2010 | Barty |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0249847 A1 | 9/2010 | Jung et al. |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0237861 A1 | 9/2011 | Pool |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0157996 A1 | 6/2012 | Walker |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0203282 A1 | 8/2012 | Sachs et al. |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2014/0005788 A1 | 1/2014 | Haaja et al. |
| 2014/0025172 A1 | 1/2014 | Lucas et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0105782 A1 | 4/2015 | D'Lima et al. |
| 2015/0105824 A1 | 4/2015 | Moskowitz et al. |

FOREIGN PATENT DOCUMENTS

| | | |
|---|---|---|
| CN | 101040807 A | 9/2007 |
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 7/2012 |
| JP | 03194208 A | 8/1991 |
| JP | H0956736 | 3/1997 |
| JP | 2002500063 A | 1/2002 |
| WO | WO1998044858 A1 | 1/2002 |
| WO | WO1999051160 A1 | 1/2002 |
| WO | WO2001024697 A1 | 1/2002 |
| WO | WO2001045485 A3 | 1/2002 |
| WO | WO2001045487 A2 | 1/2002 |
| WO | WO2001067973 A2 | 1/2002 |
| WO | WO2001078614 A1 | 1/2002 |
| WO | 20040045431 A1 | 6/2004 |
| WO | 2006090380 A2 | 8/2006 |
| WO | 2007025191 A1 | 3/2007 |
| WO | 2007118179 A2 | 10/2007 |
| WO | 2007144489 A2 | 12/2007 |
| WO | 2008003952 A1 | 1/2008 |
| WO | WO2007015239 A3 | 1/2008 |
| WO | 2008040880 A2 | 4/2008 |
| WO | WO2007013059 A3 | 4/2009 |

(56) References Cited

FOREIGN PATENT DOCUMENTS

| WO | WO2011116158 A3 | 1/2012 |
|----|-----------------|--------|
| WO | WO2013119528 A1 | 8/2013 |
| WO | WO2014040013 A1 | 3/2014 |

OTHER PUBLICATIONS

International Search Report for PCT/US2010/023780, ISA, dated Apr. 1, 2010.
Written Opinion for PCT/US2010/023780, ISA, dated Apr. 1, 2010.
Abe et al., "Experimental external fixation combined with percutaneous discectomy in the management of scoliosis.", Spine, 1999, pp. 646-653, 24, No. 7.
Ahlbom et al., "Guidelines for limiting exposure to time-varying electric, magnetic, and electromagnetic fields (up to 300 GHz). International Commission on Non-Ionizing Radiation Protection.", Health Physics, 1998, pp. 494-522, 74, No. 4.
Amer et al., "Evaluation of treatment of late-onset tibia vara using gradual angulation translation high tibial osteotomy", ACTA Orthopaedica Belgica, 2010, pp. 360-366, 76, No. 3.
Angrisani et al., "Lap-Band® Rapid Port™ System: Preliminary results in 21 patients", Obesity Surgery, 2005, p. 936, 15, No. 7.
Baumgart et al., "A fully implantable, programmable distraction nail (Fitbone)—new perspectives for corrective and reconstructive limb surgery.", Practice of Intramedullary Locked Nails, 2006, pp. 189-198.
Baumgart et al., "The bioexpandable prosthesis: A new perspective after resection of malignant bone tumors in children.", J Pediatr Hematol Oncol, 2005, pp. 452-455, 27, No. 8.
Bodó et al., "Development of a tension-adjustable implant for anterior cruciate ligament reconstruction.", Eklem Hastaliklari ve Cerrahisi—Joint Diseases and Related Surgery, 2008, pp. 27-32, 19, No. 1.
Boudjemline et al., "Off-label use of an adjustable gastric banding system for pulmonary artery banding.", The Journal of Thoracic and Cardiovascular Surgery, 2006, pp. 1130-1135, 131, No. 5.
Brown et al., "Single port surgery and the Dundee Endocone.", SAGES Annual Scientific Sessions: Emerging Technology Poster Abstracts, 2007, ETP007, pp. 323-324.
Buchowski et al., "Temporary internal distraction as an aid to correction of severe scoliosis", J Bone Joint Surg Am, 2006, pp. 2035-2041, 88-A, No. 9.
Burghardt et al., "Mechanical failure of the Intramedullary Skeletal Kinetic Distractor in limb lengthening.", J Bone Joint Surg Br, 2011, pp. 639-643, 93-B, No. 5.
Burke, "Design of a minimally invasive non fusion device for the surgical management of scoliosis in the skeletally immature", Studies in Health Technology and Informatics, 2006, pp. 378-384, 123.
Carter et al., "A cumulative damage model for bone fracture.", Journal of Orthopaedic Research, 1985, pp. 84-90, 3, No. 1.
Chapman et al., "Laparoscopic adjustable gastric banding in the treatment of obesity: A systematic literature review.", Surgery, 2004, pp. 326-351, 135, No. 3.
Cole et al., "Operative technique intramedullary skeletal kinetic distractor: Tibial surgical technique.", Orthofix, 2005.
Cole et al., "The intramedullary skeletal kinetic distractor (ISKD): first clinical results of a new intramedullary nail for lengthening of the femur and tibia.", Injury, 2001, pp. S-D-129-S-D-139, 32.
Dailey et al., "A novel intramedullary nail for micromotion stimulation of tibial fractures.", Clinical Biomechanics, 2012, pp. 182-188, 27, No. 2.
Daniels et al., "A new method for continuous intraoperative measurement of Harrington rod loading patterns.", Annals of Biomedical Engineering, 1984, pp. 233-246, 12, No. 3.
De Giorgi et al., "Cotrel-Dubousset instrumentation for the treatment of severe scoliosis.", European Spine Journal, 1999, pp. 8-15, No. 1.
Dorsey et al., "The stability of three commercially available implants used in medial opening wedge high tibial osteotomy.", Journal of Knee Surgery, 2006, pp. 95-98, 19, No. 2.
Edeland et al., "Instrumentation for distraction by limited surgery in scoliosis treatment.", Journal of Biomedical Engineering, 1981, pp. 143-146, 3, No. 2.
Elsebaie, "Single growing rods (Review of 21 cases). Changing the foundations: Does it affect the results?", Journal of Child Orthop, 2007, 1:258.
Ember et al., "Distraction forces required during growth rod lengthening.", J of Bone Joint Surg BR, 2006, p. 229, 88-B, No. Suppl. II.
European Patent Office, "Observations by a third party under Article 115 EPC in EP08805612 by Soubeiran.", 2010.
Fabry et al., "A technique for prevention of port complications after laparoscopic adjustable silicone gastric banding.", Obesity Surgery, 2002, pp. 285-288, 12, No. 2.
Fried et al., "In vivo measurements of different gastric band pressures towards the gastric wall at the stoma region.", Obesity Surgery, 2004, p. 914, 14, No. 7.
Gao et al., CHD7 gene polymorphisms are associated with susceptibility to idiopathic scoliosis, American Journal of Human Genetics, 2007, pp. 957-965, 80.
Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany, (2 pages).
Gillespie et al. "Harrington instrumentation without fusion.", J Bone Joint Surg Br, 1981, p. 461, 63-B, No. 3.
Goodship et al., "Strain rate and timing of stimulation in mechanical modulation of fracture healing.", Clinical Orthopaedics and Related Research, 1998, pp. S105-S115, No. 355S.
Grass et al., "Intermittent distracting rod for correction of high neurologic risk congenital scoliosis.", SPINE, 1997, pp. 1922-1927, 22, No. 16.
Gray, "Gray's anatomy of the human body.", http://education.yahoo.com/reference/gray/subjects/subject/128, published Jul. 1, 2007.
Grimer et al. "Non-invasive extendable endoprostheses for children—Expensive but worth it!", International Society of Limb Salvage 14th International Symposium on Limb Salvage, 2007.
Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.
Guichet et al. "Gradual femoral lengthening with the Albizzia intramedullary nail", J Bone Joint Surg Am, 2003, pp. 838-848, 85-A, No. 5.
Gupta et al., "Non-invasive distal femoral expandable endoprosthesis for limb-salvage surgery in paediatric tumours.", J Bone Joint Surg Br, 2006, pp. 649-654, 88-B, No. 5.
Hankemeier et al., "Limb lengthening with the Intramedullary Skeletal Kinetic Distractor (ISKD).", Oper Orthop Traumatol, 2005, pp. 79-101, 17, No. 1.
Harrington, "Treatment of scoliosis. Correction and internal fixation by spine instrumentation.", J Bone Joint Surg Am, 1962, pp. 591-610, 44-A, No. 4.
Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.
Hofmeister et al., "Callus distraction with the Albizzia nail.", Practice of Intramedullary Locked Nails, 2006, pp. 211-215.
Horbach et al., "First experiences with the routine use of the Rapid Port™ system with the Lap-Band®.", Obesity Surgery, 2006, p. 418, 16, No. 4.
Hyodo et al., "Bone transport using intramedullary fixation and a single flexible traction cable.", Clinical Orthopaedics and Related Research, 1996, pp. 256-268, 325.
International Commission on Non-Ionizing Radiation Protection, "Guidelines on limits of exposure to static magnetic fields." Health Physics, 2009, pp. 504-514, 96, No. 4.

(56) References Cited

OTHER PUBLICATIONS

INVIS®/Lamello Catalog, 2006, Article No. 68906A001 GB.
Kasliwal et al., "Management of high-grade spondylolisthesis.", Neurosurgery Clinics of North America, 2013, pp. 275-291, 24, No. 2.
Kenawey et al., "Leg lengthening using intramedullay skeletal kinetic distractor: Results of 57 consecutive applications.", Injury, 2011, pp. 150-155, 42, No. 2.
Kent et al., "Assessment and correction of femoral malrotation following intramedullary nailing of the femur.", Acta Orthop Belg, 2010, pp. 580-584, 76, No. 5.
Klemme et al., "Spinal instrumentation without fusion for progressive scoliosis in young children", Journal of Pediatric Orthopaedics. 1997, pp. 734-742, 17, No. 6.
Korenkov et al., "Port function after laparoscopic adjustable gastric banding for morbid obesity.", Surgical Endoscopy, 2003, pp. 1068-1071, 17, No. 7.
Krieg et al., "Leg lengthening with a motorized nail in adolescents.", Clinical Orthopaedics and Related Research, 2008, pp. 189-197, 466, No. 1.
Kucukkaya et al., "The new intramedullary cable bone transport technique.", Journal of Orthopaedic Trauma, 2009, pp. 531-536, 23, No. 7.
Lechner et al., "In vivo band manometry: A new method in band adjustment", Obesity Surgery, 2005, p. 935, 15, No. 7.
Lechner et al., "Intra-band manometry for band adjustments: The basics", Obesity Surgery, 2006, pp. 417-418, 16, No. 4.
Li et al., "Bone transport over an intramedullary nail: A case report with histologic examination of the regenerated segment", Injury, 1999, pp. 525-534, 30, No. 8.
Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering•General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering . . . can it work?.", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, p. 511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany, (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013, Vancouver, Canada. Scoliosis Research Society.
Sun et al., "Masticatory mechanics of a mandibular distraction osteogenesis site: Interfragmentary micromovement", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children,", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.

(56) References Cited

OTHER PUBLICATIONS

Thonse et al., "Limb lengthening with a fully implantable, telescopic, intramedullary nail.", Operative Techniques in Orthopedics, 2005, pp. 355-362, 15, No. 4.

Trias et al., "Dynamic loads experienced in correction of idiopathic scoliosis using two types of Harrington rods.", Spine, 1979, pp. 228-235, 4, No. 3.

Verkerke et al., "An extendable modular endoprosthetic system for bone tumor management in the leg", Journal of Biomedical Engineering, 1990, pp. 91-96, 12, No. 2.

Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.

Verkerke et al., "Development and test of an extendable endoprosthesis for bone reconstruction in the leg.", The International Journal of Artificial Organs, 1994, pp. 155-162, 17, No. 3.

Weiner et al., "Initial clinical experience with telemetrically adjustable gastric banding", Surgical Technology International, 2005, pp. 63-69, 15.

Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.

White, III et al., "The clinical biomechanics of scoliosis.", Clinical Orthopaedics and Related Research, 1976, pp. 100-112, 118.

Yonnet, "A new type of permanent magnet coupling.", IEEE Transactions on Magnetics, 1981, pp. 2991-2993, 17, No. 6.

Yonnet, "Passive magnetic bearings with permanent magnets.", IEEE Transactions on Magnetics, 1978, pp. 803-805, 14, No. 5.

Zheng et al., "Force and torque characteristics for magnetically driven blood pump.", Journal of Magnetism and Magnetic Materials, 2002, pp. 292-302, 241, No. 2.

\* cited by examiner

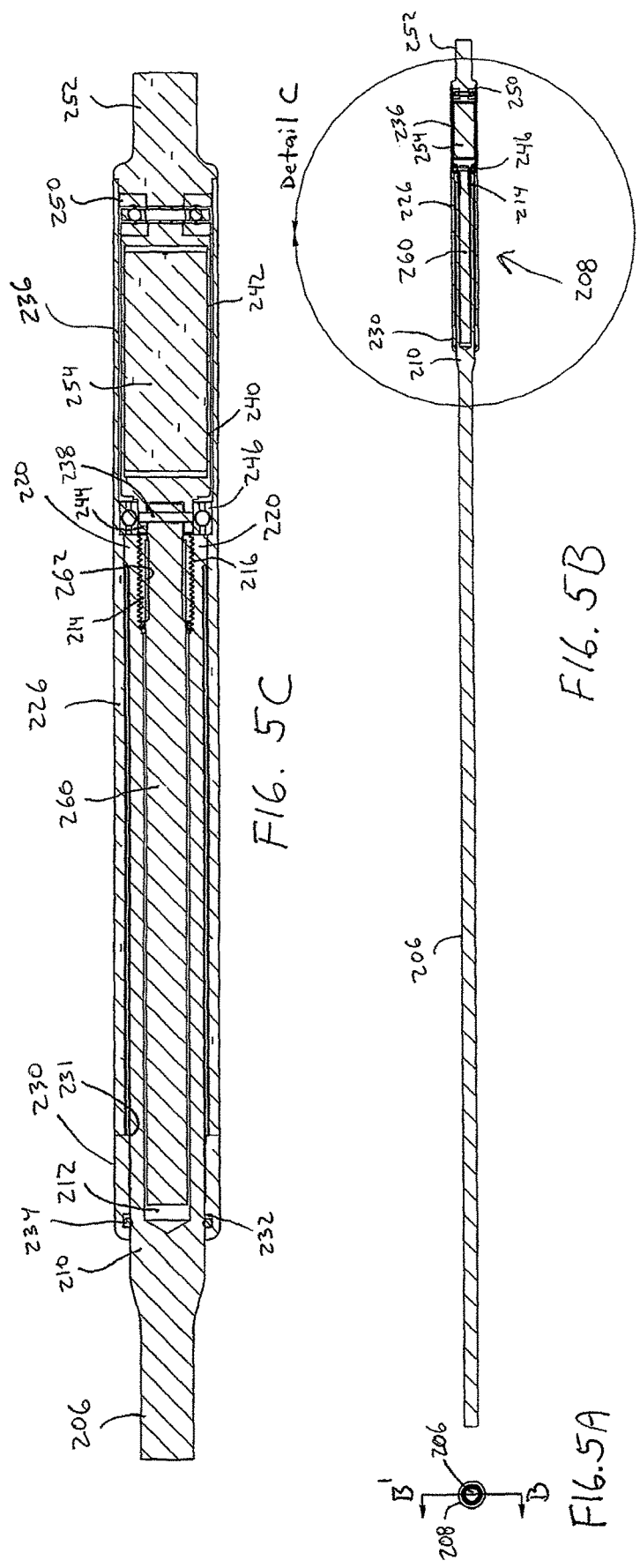

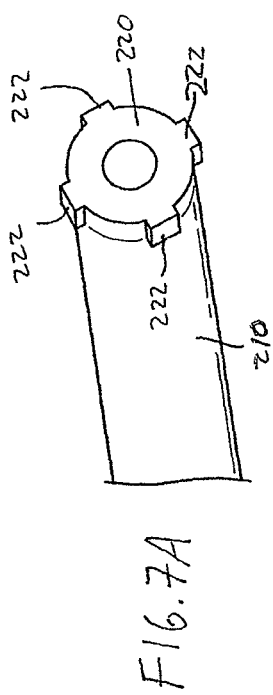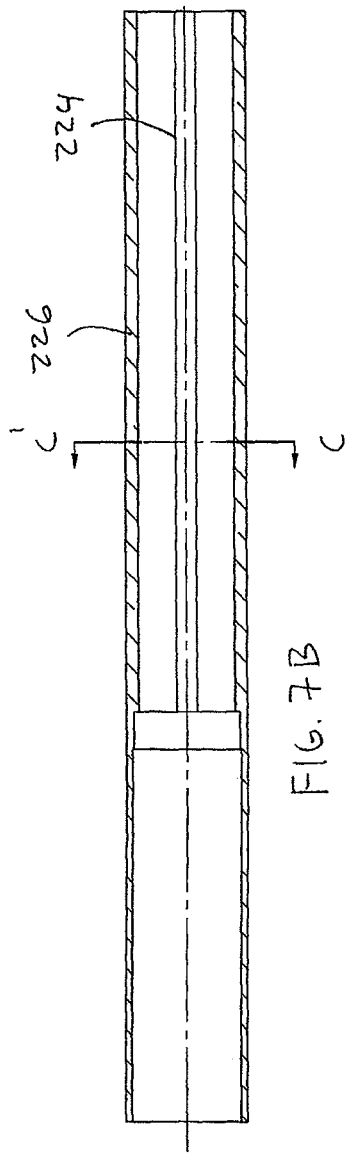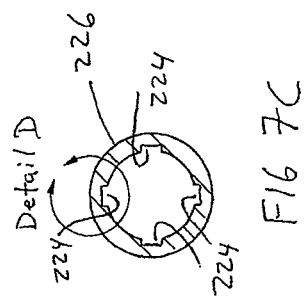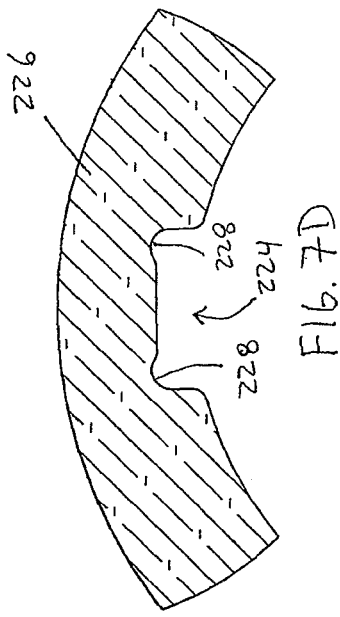

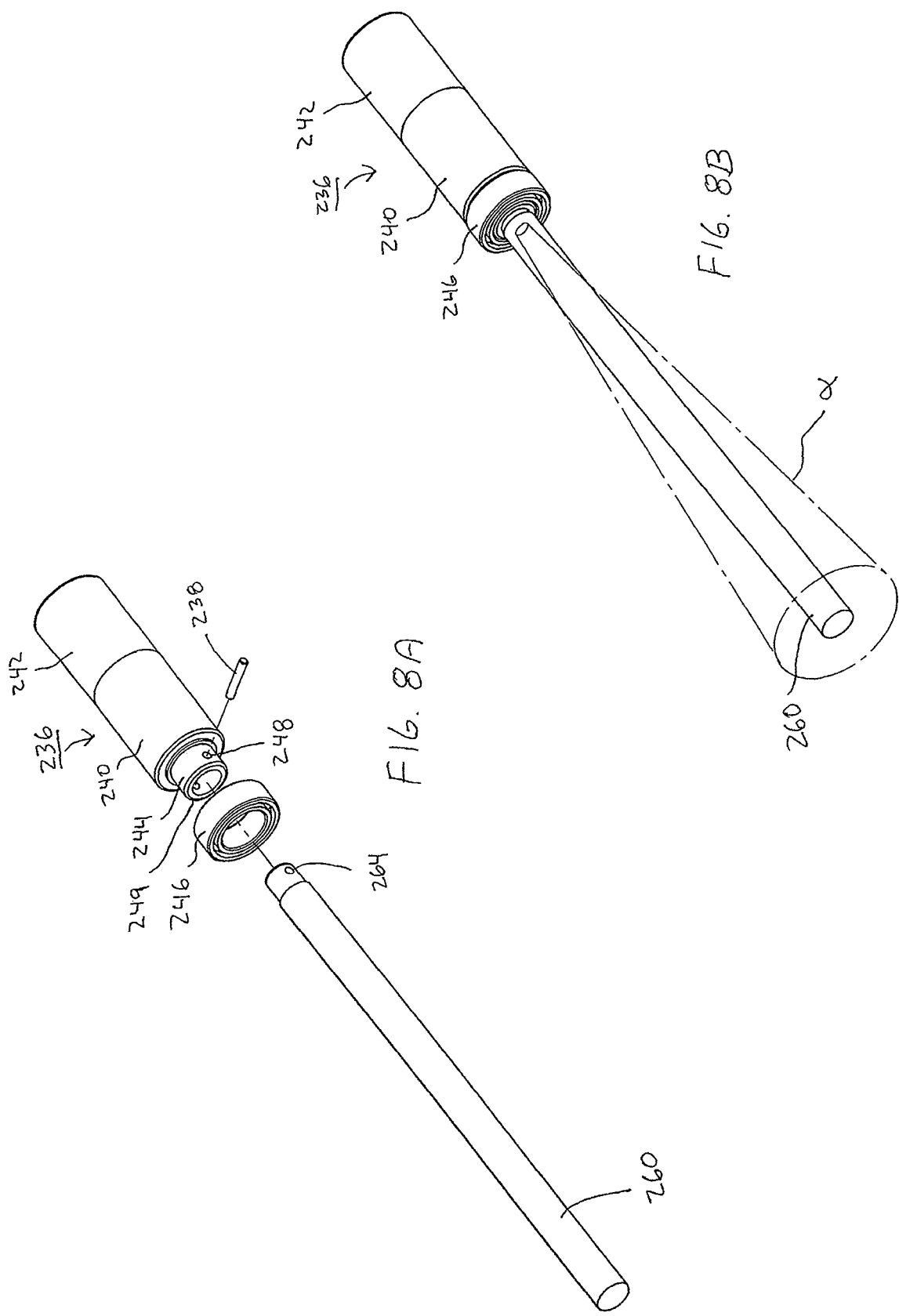

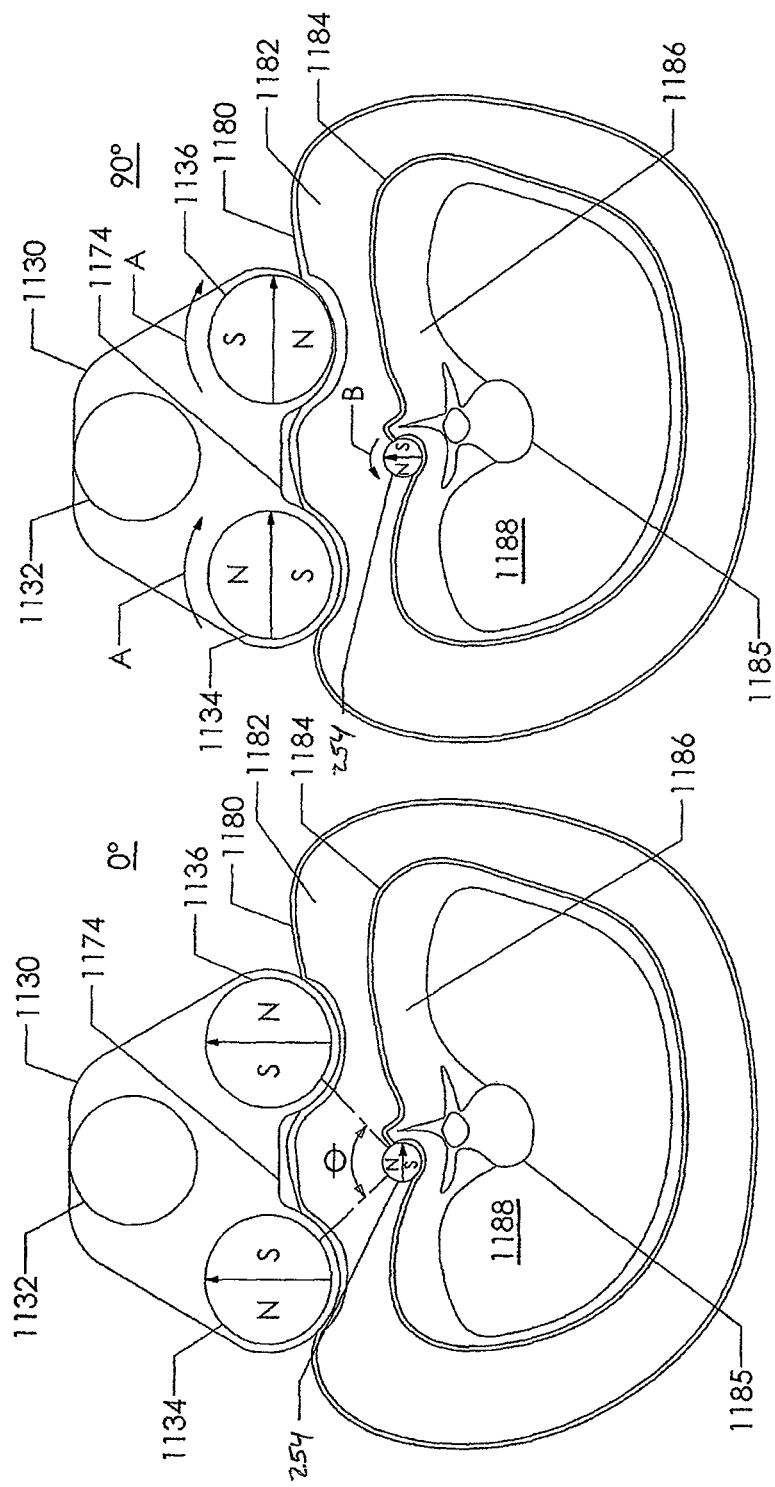

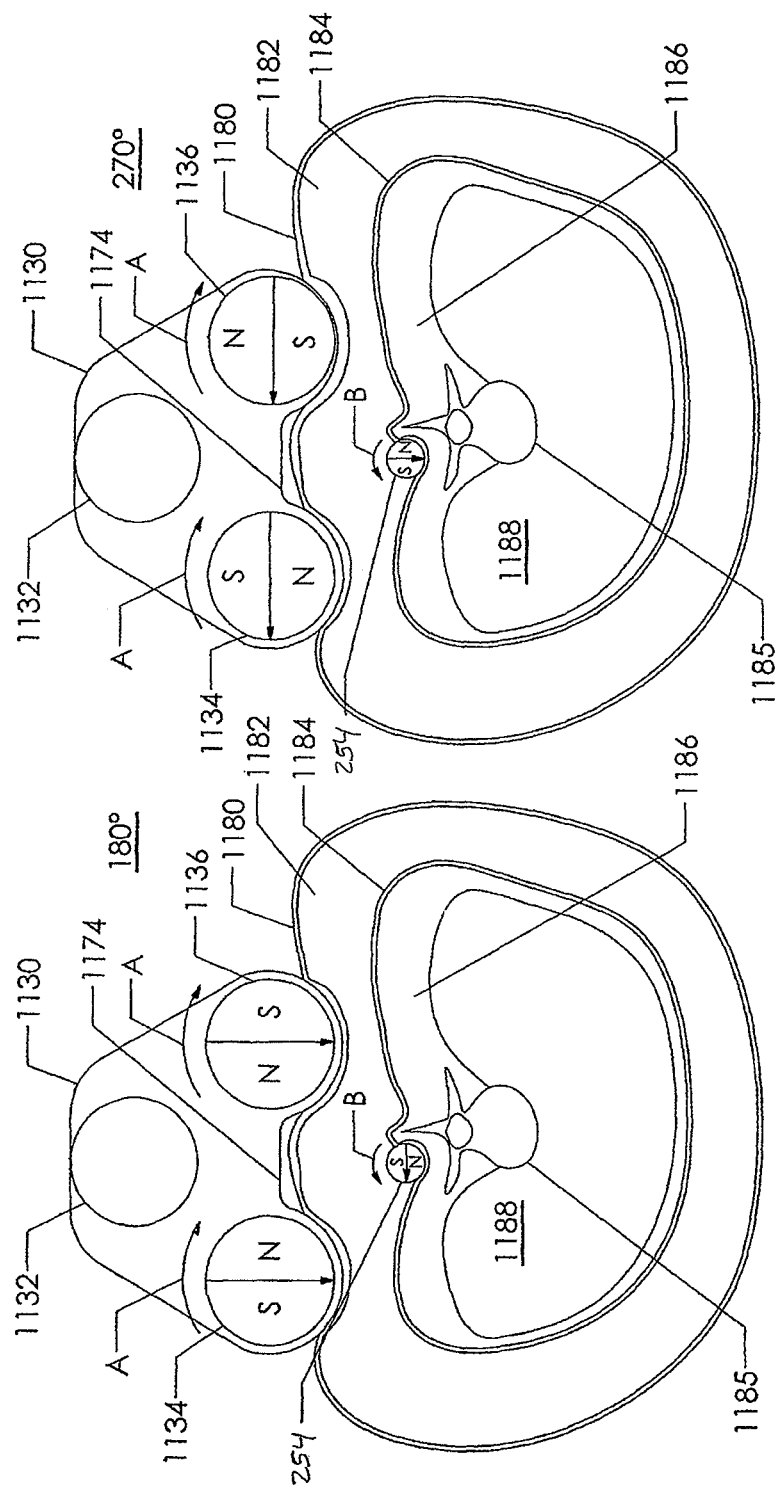

NON-INVASIVE ADJUSTABLE DISTRACTION SYSTEM

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE INVENTION

The field of the invention generally relates to medical devices for treating disorders of the skeletal system.

BACKGROUND OF THE INVENTION

Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. There is a large population of grown adults with untreated scoliosis, in extreme cases with a Cobb angle as high as or greater than 90°. Many of these adults, though, do not have pain associated with this deformity, and live relatively normal lives, though oftentimes with restricted mobility and motion. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with hooks or bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

In some cases, after surgery, the patient will wear a protective brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twisting. As these fused patients mature, the fused section can impart large stresses on the adjacent non-fused vertebra, and often, other problems including pain can occur in these areas, sometimes necessitating further surgery. This tends to be in the lumbar portion of the spine that is prone to problems in aging patients. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five, and more often in boys than in girls. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection.

Returning to the AIS patients, the treatment methodology for those with a Cobb angle between 20° and 40° is quite controversial. Many physicians proscribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spine. Currently a prospective, randomized 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery.

Many physicians feel that the BrAIST trial will show that braces are completely ineffective. If this is the case, the quandary about what to do with AIS patients who have a Cobb angle of between 20° and 40° will only become more pronounced. It should be noted that the "20° to 40°" patient population is as much as ten times larger than the "40° and greater" patient population.

Currently, genetic scientists are at work to find one or more genes that may predispose scoliosis. Once identified, some are still skeptical as to whether gene therapy would be possible to prevent scoliosis, however the existence of a scoliosis gene would no doubt allow for easier and earlier identification of probable surgical patients.

SUMMARY OF THE INVENTION

In a first embodiment, a spinal distraction system includes a distraction rod having a first end and a second end, the first end being configured for affixation to a subject's spine at a first location, the distraction rod having a second end containing a recess having a threaded portion disposed therein. The distraction system further includes an adjustable portion configured for placement relative to the subject's spine at a second location remote from the first location, the adjustable portion comprising a housing containing a magnetic assembly, the magnetic assembly affixed at one end thereof to a lead screw via a locking pin passing transversely through the lead screw, the lead screw operatively coupled to the threaded portion.

In a second embodiment, a spinal distraction system includes a distraction rod having a first end and a second end, the first end being configured for affixation to a subject's spine at a first location, the distraction rod having a second end containing a recess having a threaded portion disposed therein. The adjustable portion is configured for placement relative to the subject's spine at a second location remote from the first location, the adjustable portion includes a housing containing a magnetic assembly, the magnetic assembly affixed at one end thereof to a lead screw, the lead screw operatively coupled to the threaded portion. The system further includes a recess disposed in an interior portion of the housing adjacent to one end, the recess having at least one o-ring therein dimensioned to form a fluid tight seal with the distraction rod.

BRIEF DESCRIPTION OF THE DRAWINGS

FIG. 5A is a cross-sectional view of a distraction rod and adjustable portion taken along a perpendicular axis to the longitudinal axis of the distraction rod.

FIG. 5B illustrates a cross-sectional view of the distraction rod and the adjustable portion taken along the line B'-B of FIG. 5A.

FIG. 5C illustrates an enlarged cross-sectional view of detail C of FIG. 5B.

FIG. 7A illustrates a perspective view of one end of a distraction rod illustrating the splined tip.

FIG. 7B is a side cross-sectional view of the tubular housing with the lead screw and magnetic assembly removed for clarity.

FIG. 7C is a cross-sectional view of the tubular housing taken along the line C'-C in FIG. 7B.

FIG. 7D illustrates a magnified view of detail D of FIG. 7C.

FIG. 8A is an exploded perspective view of the magnetic assembly, locking pin, bearing, and lead screw.

FIG. 8B is a perspective view illustrating the magnetic assembly coupled to the lead screw via the locking pin (hidden by the bearing). The off axis wiggle of the lead screw is illustrated by the cone-shaped envelope a.

FIG. 13A illustrates a cross-sectional representation of the external adjustment device being positioned on a patient's skin. FIG. 13A illustrates the permanent magnet in the 0° position.

FIG. 13B illustrates a cross-sectional representation of the external adjustment device being positioned on a patient's skin. FIG. 13B illustrates the permanent magnet in the 90° position.

FIG. 13C illustrates a cross-sectional representation of the external adjustment device being positioned on a patient's skin. FIG. 13C illustrates the permanent magnet in the 180° position.

FIG. 13D illustrates a cross-sectional representation of the external adjustment device being positioned on a patient's skin. FIG. 13D illustrates the permanent magnet in the 270° position.

DETAILED DESCRIPTION OF THE ILLUSTRATED EMBODIMENTS

Figure 1:
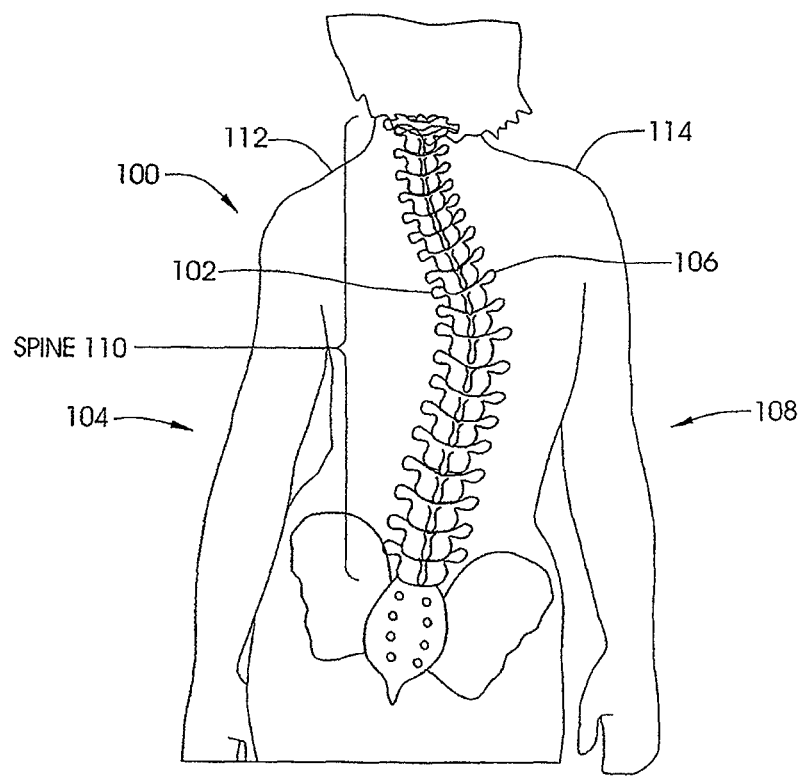
FIG. 1 illustrates the spine of a person with scoliosis.

FIG. 1 illustrates a patient 100 with scoliosis. The concave portion 102 of the spinal curve can be seen on the left side 104 of the patient 100, and the convex portion 106 can be seen on the right side 108 of the patient 100. Of course, in other patients, the concave portion 102 may appear on the right side 108 of the patient 100 while the convex portion 106 may be found on the left side 104 of the patient. In addition, as seen in FIG. 1, some rotation of the spine 110 is present, and unevenness between the left shoulder 112 and right shoulder 114 is seen.

Figure 2:
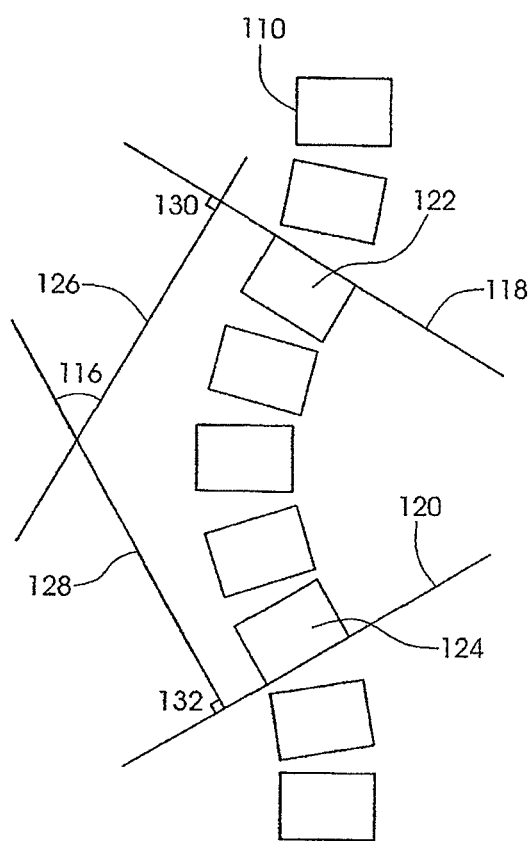
FIG. 2 illustrates the Cobb angle of a scoliotic spine.

FIG. 2 illustrates the Cobb angle 116 of a spine 110 of a patient with scoliosis. To determine the Cobb angle, lines 118 and 120 are drawn from vertebra 122 and 124, respectively. Intersecting perpendicular lines 126 and 128 are drawn by creating 90° angles 130 and 132 from lines 118 and 120. The angle 116 created from the crossing of the perpendicular lines 126 and 128 is defined as the Cobb angle. In a perfectly straight spine, this angle is 0°.

Figure 3:
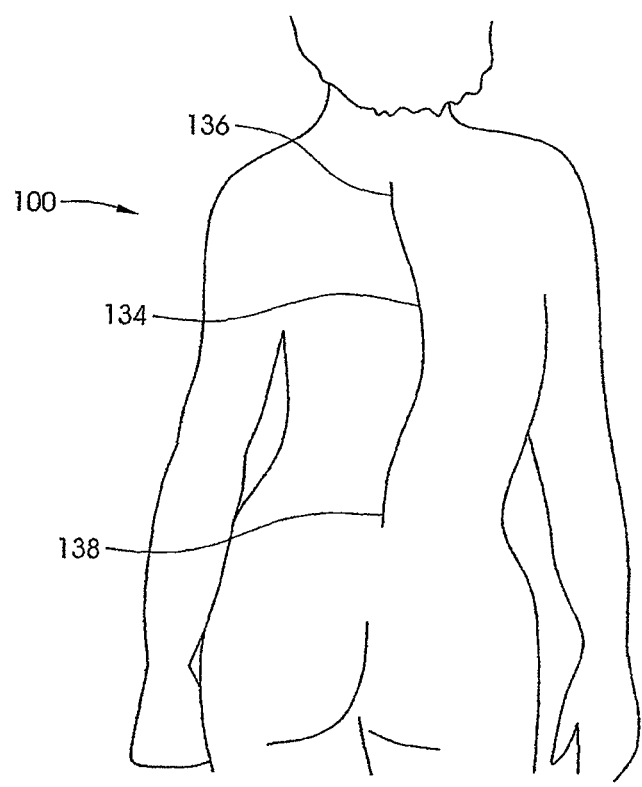
FIG. 3 illustrates the large incision made during prior art scoliosis fusion surgery.

In many Adolescent Idiopathic Scoliosis (AIS) patients with a Cobb angle of 40° or greater, spinal fusion surgery is typically the first option. FIG. 3 illustrates a long incision 134 formed in the patient 100 which is typically made during posterior scoliosis fusion surgery. This type of fusion surgery is known in the prior art. The long incision 134 extends between an upper end 136 and a lower end 138. The length of this incision 134 is longer than the length of the section of the vertebra to be fused. The actual length between the upper end 136 and the lower end 138 varies, depending on the size of the patient, and the extent of the scoliosis, but in AIS patients this length is significantly longer than 15 cm. More typically, it is longer than 25 cm.

Figure 4:
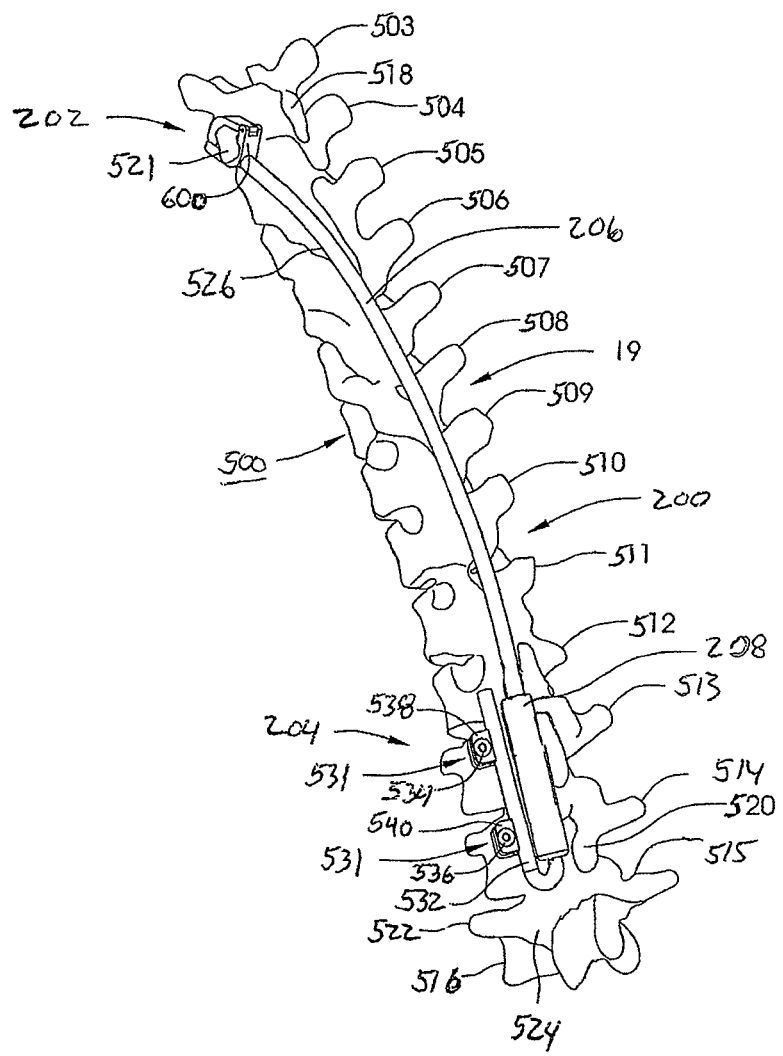
FIG. 4 illustrates an exemplary distraction device mounted on the spine of a subject.

FIG. 4 illustrates a distraction device 200 for treating scoliosis according to one embodiment of the invention. The distraction device 200, which is an implantable device, is fixated at its upper end 202 and lower end 204 to the patient's spine 500. The illustrated example of the spine 500 includes the particular thoracic and lumbar vertebrae that typically encompass a scoliotic curve, for example the curve of a patient with adolescent idiopathic scoliosis. The T3 through T12 thoracic vertebrae, 503, 504, 505, 506, 507, 508, 509, 510, 511, 512, respectively and the L1 through L3 vertebrae, 513, 514, 515 are depicted in FIG. 4, not in a severe scoliotic condition, but in a very slight residual curve that represents a modest curve that has been partially or completely straightened during the implantation procedure.

Each vertebra is different from the other vertebra by its size and shape, with the upper vertebra generally being smaller than the lower vertebra. However, generally, the vertebrae have a similar structure and include a vertebral body 516, a spinous process 518, 520, laminae 526, transverse processes 521, 522 and pedicles 524. In this embodiment, the distraction device 200 includes a distraction rod 206 which is adjustable (lengthwise) via a coupled adjustable portion 208. The distraction device 200 is fixated to the spine 500 via a clamp 600 at the upper end 202 of the distraction rod 206. In FIG. 4, the clamp 600 is secured around the transverse process 521 of the T4 vertebra 504. Alternatively, the clamp 600 may be secured around an adjacent rib (not shown) or rib facet. In still another alternative, the clamp may be replaced by a laminar and pedicle hook system, or pedicle screw system. Exemplary pedicle hook systems or pedicle screw systems may be found in U.S. patent application Ser. Nos. 12/121,355 and 12/250,442 which are incorporated by reference as if set forth fully herein.

Referring back to FIG. 4, the distraction device 200 is illustrated as being fixated to the spine 500 with a pedicle screw system 531 comprising a connecting rod 532 and two toe clamps 538, 540. The connecting rod 532 is shown curving back on itself in the shape of a "J." The connecting rod 532 then interfaces with the adjustable portion 208. As explained in more detail below. The adjustable portion 208 preferably contains a magnetic assembly having a permanent magnet configured to drive a lead screw that, depending on the direction of rotation of the internal magnet, will extend or retract the distraction rod 206 using the adjustable portion 208. Lengthening of the distraction rod 206, for example, will impart a distraction force to the spine 500. Retracting the distraction rod 206 will lower or remove the distraction force on the spine 500, for example if too high a distraction force causes pain or complications.

Still referring to FIG. 4, a locking screw 534 can be loosened to adjust the angle of the connecting rod 532 into the desired orientation and then locking screw 534 can be tightened so that toe clamp 538 securely holds connecting rod 532 in place without further rotation. The second toe clamp 540 is adjusted in the same way, by tightening locking screw 536. Because a scoliotic spine is also rotated (usually the center section is rotated to the right in AIS patients), the non-fusion embodiment presented here allows de-rotation of the spine 500 to happen naturally, because there is no fixation at the middle portion of the distraction device 200.

In order to further facilitate this de-rotation, the distraction device 200 may allow for free rotation at its ends. For example, the adjustable portion 208 may be coupled to the connecting rod 532 via an articulating joint. U.S. patent application Ser. Nos. 12/121,355 and 12/250,442 describe various articulating interfaces and joints that may be utilized to couple the adjustable portion 108 to the connecting rod 532 or the like.

It should be noted that distraction rod 206 may be precurved with the typical shape of a normal saggital spine, but it should also be noted that the curve may be slightly different than standard scoliosis fusion instrumentation, because in the non-fusion embodiment described herein, the distraction device 200 is not flush with the spine but rather is placed either subcutaneous or sub-fascial, and thus is not below the back muscles. The only portions of the distraction device 200 that are designed to be placed below the muscles are the clamp 600 and the portion of the distraction rod 206 immediately adjacent the clamp 600, the pedicle screw system 531 and the connecting rod 532. Thus, FIG. 4 illustrates an embodiment in which the bulk of the hardware associated with the distraction device 200 is placed over the muscle. It should be understood, however, that in alternative configurations, any other part of the entire implantable embodiment may be placed under the muscle (i.e., submuscular). It should be appreciated that a much smaller amount of muscle needs to be dissected during the procedure in comparison with current fusion procedures. This will allow for a much shorter procedure, much less blood loss, much quicker recovery, and less time in the hospital/less risk of infection. Further, it may be desirable to produce the "J" curve of the connecting rod 532 or any other curve at the connecting rod 532 with optional flanges or ribs at their highest stress points in order to increase their durability in demanding implant conditions.

FIGS. 5A-5C illustrate cross-sectional views of the interface of the distraction rod 206 with the adjustable portion 208. FIG. 5A is a cross-sectional view of the distraction rod 206 and adjustable portion 208 taken along a perpendicular axis to the longitudinal axis of the distraction rod 206. FIG. 5B illustrates a cross-sectional view of the distraction rod 206 and the adjustable portion 208 taken along the line B'-B of FIG. 5A. FIG. 5C illustrates an enlarged cross-sectional view of detail C of FIG. 5B. As best seen in FIG. 5C, an end 210 of the distraction rod 206 includes an elongate recess 212. The elongate recess 212 may have a length of around 60 mm The recess 212 is dimensioned to receive a lead screw 260. The lead screw 260 may be made from a high strength material such as, for example, titanium. At least a portion of the lead screw 260 includes external threads 262 that are configured to engage with a nut 214 integrated into the recess 212. The nut 214 provides a threaded portion on the recess 212 of the distraction rod 206. The lead screw 260 may have, for example, 80 threads per inch although more or less could be used. The nut 214 may include threads or a chamfered surface 216 on the outer diameter in order to better ensure a secure attachment to the inner diameter of the recess 212 of the distraction rod 206. For example, the nut 214 may be bonded to the distraction rod 206 using an adhesive such as EPOTEK 353ND, available from EPDXY TECHNOLOGY, INC., 14 Fortune Drive, Billerica, Mass. This allows the distraction rod 206 to be fabricated from a single piece of stronger material. It also provides for clearance between the lead screw 260 and internal diameter of the distraction rod 206. Alternatively, a threaded portion may be directly formed in the recess 212 without the aid of a separate nut 214.

Figure 6A:
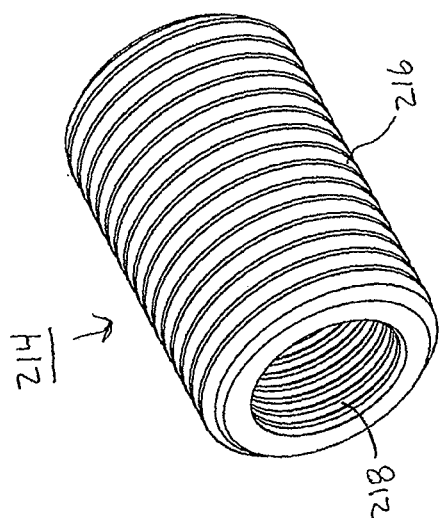
FIG. 6A illustrates a perspective view of a nut disposed within an interior recess located at one end of the distraction rod.
Figure 6C:
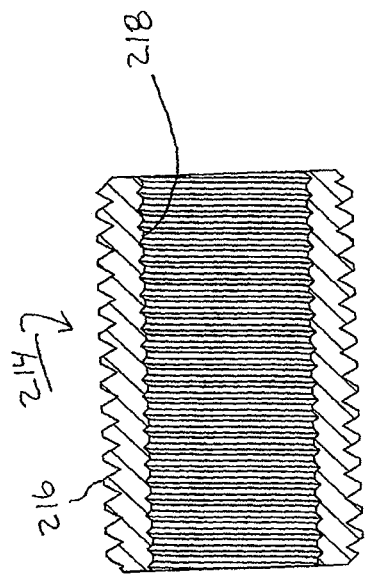
FIG. 6C is a cross-sectional view of the nut taken along the line C-C of FIG. 6B.
Figure 6B:
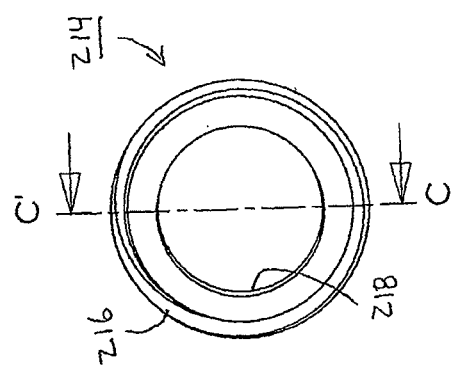
FIG. 6B is an end view of the nut of FIG. 6A.

FIGS. 6A-6C illustrate separate views of the nut 214. The nut includes internal threads 218 that engage with the outer threads 262 of the lead screw 260. In one aspect, the nut 214 is made from aluminum-bronze #630. By using dissimilar metals (titanium for lead screw 260 and aluminum-bronze for the nut 214) with different hardness values results in less gall/bind between the lead screw 260 and the nut 214. This further enables to the lead screw 260 and the nut 214 to operate with reduced friction. Optionally, various wet or dry lubricants may be used to reduce friction between the lead screw 260 and the nut 214. One example of a wet lubricant includes biocompatible silicone oil such as MED-360 (100, 000 cp) available from NuSil Technology, 1050 Cindy Lane, Carpinteria, Calif. 93013.

Referring back to FIG. 5C, the end of the distraction rod 206 includes a splined tip 220 that includes one or more protrusions 222 that interface with corresponding longitudinal grooves 224 (not shown in FIG. 5C) disposed within an inner surface of a tubular housing 226. FIG. 7A illustrates a perspective view of the splined tip 220. The splined tip 220 is illustrated with four (4) protrusions 222 that interface with four (4) corresponding longitudinal grooves 224 (two pairs in symmetric opposition) formed inside a tubular housing 226 (illustrated in FIGS. 7B-D). The longitudinal grooves 224 may be formed by wire EDM machining. While FIGS. 7A-7D illustrate an embodiment that uses four (4) protrusions 222 along with four (4) longitudinal grooves 224 there may be more or less. The tight tolerance of the splined tip 220 with the longitudinal grooves 224 keeps the distraction rod 206 centered within the tubular housing 226. In addition, the combination of the splined tip 220 and corresponding grooves 224 act as an anti-rotation feature that prevents the distraction rod 206 from rotating relative to the tubular housing 226. This may be necessary to allow the distraction device 200 to be "rigidized" in the event the device is used in fusion applications, instead of the non-fusion applications described. For example, in a fusion application, it is desired that the spine 500 not be able to flex or rotate much during the months that the fusion is taking place. In either the fusion applications or the non-fusion applications, the anti-rotation features prevent inadvertent extension and/or retraction of the distraction rod 206 resulting from, for instance, patient movements.

FIG. 7C is a cross-sectional view of the tubular housing 226 taken along the line C-C in FIG. 7B. FIG. 7D illustrates a magnified view of detail D of FIG. 7C. In this illustrated embodiment, as best seen in the detailed view of FIG. 7D, small reliefs 228 are incorporated into the sides or corners of the longitudinal grooves 224. These reliefs 228 may be slight over cut wire EDM notches that prevent the corners of the protrusions 222 from contacting the inner wall of the tubular housing 226. Less contact between the protrusions 222 and the longitudinal grooves 224 results in less frictional forces and reduces the likelihood of binding. Optionally, the tops of the protrusions 222 could be curved, for example, cut from a diameter instead of a square. This rounding of the protrusions 222 would keep the protrusions 222 from binding with the longitudinal grooves 224 when torsional stresses are imparted between the distraction rod 206 and the adjustable portion 208. This optional modification makes the distraction rod 106 easier to manufacture and eliminates the need for the relief 228 overcuts.

Referring back to FIGS. 5B and 5C, an o-ring gland 230 is affixed or otherwise bonded to an end of the tubular housing 226. The o-ring gland 230 is, for example, electron beam (e-beam) or laser welded to the end of the tubular housing 226. As best illustrated in FIG. 5C, the o-ring gland 230 has an inner diameter than is less than inner diameter of the tubular housing. In this regard, a stop 231 is created that prevents further advancement of the splined tip 220 from exiting the tubular housing 226. This will assure that the distraction rod 206 cannot be over-distracted in relation to the adjustable portion 208, and thus that integrity is maintained (e.g., the distraction rod 206 does not disconnect or jam). The o-ring gland 230 further includes a recess 232 that is dimensioned to receive an o-ring 234. The o-ring 234 may be formed from a biocompatible material such as 70 durometer ethylene propylene diene M-class rubber (EPDM) available from Precision Associates, Inc., 740 North Washington Ave., Minneapolis, Minn., 55401-1188. The o-ring 234 may have an inner diameter of around 0.241 inches +/−0.005 inches with a cross-section of 0.030 inches +/−0.003 inches. The outer diameter of the end 210 of the distraction rod 206 may be around 0.25 inches. A biocompatible lubricant such as biocompatible silicone oil (e.g., MED-360 available from NuSil Technology) may be applied to the o-ring 234. The o-ring 234 thus forms a fluid-tight seal with the outer surface of the distraction rod 206.

Thus, the distraction rod 206 is able to telescope relative to the housing 226 while simultaneously preventing foreign matter from entering the housing 226. While a single o-ring 234 is illustrated in FIG. 5C, multiple o-rings may also be used to provide additional confidence in seal integrity. With respect to the single o-ring 234 illustrated in FIG. 5C, the radial compression of the o-ring is greater than 7%, and preferably falls within the range between about 13% to 18%. Further, the fill volume of the recess 232 of the o-ring gland 230 is designed to be less than 75% in all cases and more particularly, within a range of about 40% to about 54%. It is desired to have all surfaces that contact the o-ring 234 be smooth. For example, the recess 232 may be designed with a smooth surface finish. Rough finishes can damage the o-ring 234 or provide a potential leakage path across sealing surfaces. An exemplary surface finish is 16 microinches RMS.

The o-ring 234 may provide several advantages in keeping foreign materials out of the tubular housing 226. In particular, positive air pressure within the tubular housing 226 may be created during the manufacturing process. The positive air pressure provides additional stored pushing force to aid in distraction of the distraction rod 206. The positive air pressure also aids in preventing ingress of foreign matter. The use of the o-ring 234 within the recess 232 of the o-ring gland 230 permits telescopic movement of the distraction rod 206 while at the same time seals in the interior of the tubular housing 226 from the exterior environment. In vivo animal testing has confirmed that such an arrangement has maintained the integrity of the tubular housing 226 for over seven months. In a seven month study conducted in vivo in pigs, the distraction device 200 was removed and the adjustable portion 208 was fully functional.

As best seen in FIGS. 5C, 8A, 8B, the distraction rod 206 is coupled to a magnetic assembly 236 via a locking pin 238. The lead screw 260 contains an aperture 264 transversely oriented with respect to the longitudinal axis of the lead screw 260 at the proximal end that is dimensioned to receive the locking pin 238. The magnetic assembly 236, which is described in more detail below, includes an upper cup 240 and a lower cup 242. The upper cup 240 terminates at a receptacle 244 that has an inner diameter dimensioned to receive the end of the lead screw 260 containing the aperture 264. The receptacle 244 also has an outer diameter that interfaces with an interior surface a bearing 246. The bearing 246 may include a radial ball bearing that rotatably holds the upper cup 240 (via the receptacle 244) within the tubular housing 226. The receptacle 244 includes apertures 248, 249 through which the locking pin 238 is placed to lock the lead screw 260 to the magnetic assembly 236. The locking pin 238 remains in place because, when in place, the bearing 246 prevents the locking pin 238 from sliding out of the apertures 248, 249 in the receptacle 244. This overlap also advantageously shortens the overall length of the magnetic assembly 236. Alternatively, only a single aperture 248 may be used and the opposing end of the locking pin 238 may interface with a recess located on the opposing side of the receptacle 244.

The interface between the lead screw 260 and the magnetic assembly 236 has several functions. The interface must withstand heavy compressive loads. It also may need to withstand large tensile loads. Furthermore, the interface must transmit torque from the rotating magnetic assembly 236 to the lead screw 260. The interface must also maintain the concentric alignment between the lead screw 260 and the nut 214. With respect to compressive loads, these are transmitted down the lead screw 260 and across the locking pin 238 and into the magnetic assembly 236. The magnetic assembly 236, as best seen in FIG. 5C, rides on a thrust ball bearing 250. An end cap 252 located at one end of the tubular housing 226 is provided. The end cap 252 may be laser or e-beam welded to the tubular housing 226. The end cap 252 may be used to couple or otherwise interface with a joint (e.g., articulating joint) that is coupled or otherwise connected to, for example, a connecting rod 532 such as that illustrated in FIG. 4.

With respect to tensile loads, these are transmitted from the magnetic assembly 236 across the locking pin 238 and up the lead screw 260. The locking pin 238 pulls on the magnetic assembly which is retained by the bearing 246. The locking pin 238 may be made from a strong material such as, for instance, 440C stainless steel that has been heat treated for added strength. For instance, the 440C stainless steel may be heated to achieve a hardness of at least C58 Rockwell. The locking pin 238 may have a length of around 0.185 inches and a diameter of around 0.0314 inches. The ends of the locking pin 238 may be beveled. The ultimate pull strength at which the locking pin 238 fails has been determined in testing to be 353 lbs. Thus, the locking pin 238 retains its structural integrity up to a tensile load force of about 350 lbs. This is significantly higher than the highest expected distraction force. For example, other researchers have found that peak distraction forces experienced by growing rods are at or less than 124 lbs. See Teli et al., Measurement of Forces Generated During Distraction of Growing Rods, J. Child Orthop 1:257-258 (2007). The locking pin 238 described herein thus provides a wide margin of safety given the anticipated distraction forces that are experienced by the distraction rod 206.

Torquing forces are transmitted from the magnetic assembly 236 to the lead screw 260 via the locking pin 238. Because the torque available is limited, even small mechanical losses due to component binding is a problem. Here, however, the clearances between the locking pin 238 and the lead screw 260 allow the lead screw 260 to "wiggle" freely in the upper cup 240 of the magnetic assembly 236. FIG. 8B illustrates the cone-shaped envelope a traced by the off axis "wiggle" permitted by the interface of the locking pin 238 with the lead screw 260. This wiggle or play allows the lead screw 260 and nut 214 to self-align to reduce binding.

Figure 9B:
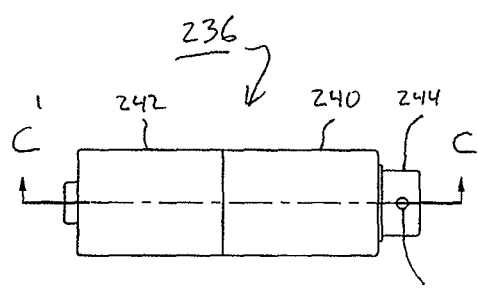
FIG. 9B is a side view of the magnetic assembly.
Figure 9A:
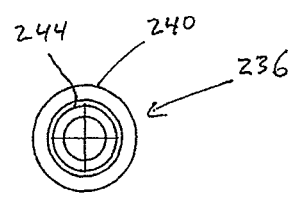
FIG. 9A is an end view of the magnetic assembly.
Figure 9C:
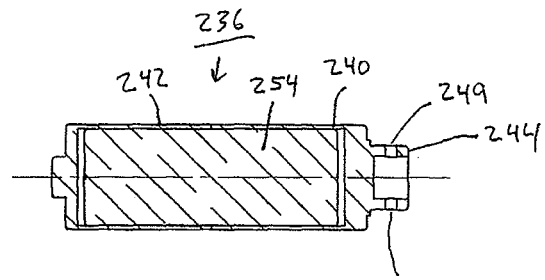
FIG. 9C is a cross-sectional view of the magnetic assembly illustrated in FIG. 9B taken along the line C-C.

FIGS. 9A-9C illustrate the magnetic assembly 236. FIG. 9A illustrates an end view of the magnetic assembly 236 while FIG. 9B illustrates a side view of the magnetic assembly 236. FIG. 9C is a cross-sectional view of the magnetic assembly 236 taken along the line C-C of FIG. 9B. The magnetic assembly 236, as explained above, includes an upper cup 240 and a lower cup 242. A permanent magnet 254 is located in the recess formed between the interior portions of the upper cup 240 and the lower cup 242. The permanent magnet 254 is preferably a cylindrical magnet having a diameter of about 0.28 inches and a length of about 0.73 inches although other dimensions may be used. The permanent magnet 254 may include, for example, a rare earth magnet formed from, for instance, Neodynium-Iron-Boron. The magnet may be made from a grade of N35 or higher, for example a grade of N50. The permanent magnet 254 is bonded or otherwise affixed to the upper cup 240 and the lower cup 242. An epoxy adhesive such as EPOTEK 353ND may be used to bond the permanent magnet 254 to the upper cup 240 and the lower cup 242. This allows torque applied to the permanent magnet 254 to be transferred to the upper cup 240 and thus the lead screw 260. The permanent magnet 254 is shorter in length than the combined lengths of the internal cavities of the upper cup 240 and lower cup 242. This assures that when the magnetic assembly 236 is under compression, the upper cup 240 and the lower cup 242 are stressed instead of the permanent magnet 254.

Figure 10:
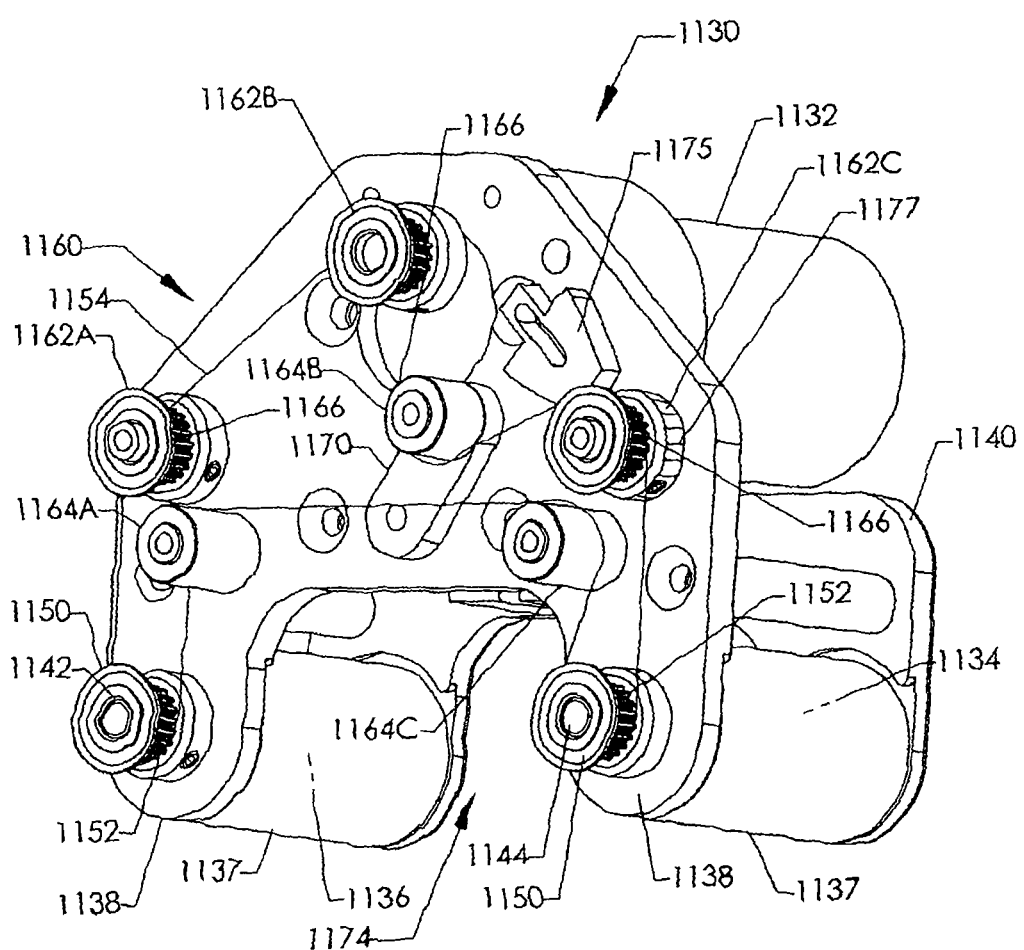
FIG. 10 illustrates a perspective view of an external adjustment device according to one embodiment. The outer housing or cover is removed to illustrate the various aspects of the external adjustment device.

FIG. 10 illustrates an external adjustment device 1130 that may be used to externally impart rotational motion or "drive" the magnetic assembly 236 located within the distraction device 200. The external adjustment device 1130 includes a motor 1132 that is used to impart rotational movement to two permanent magnets 1134, 1136. The two permanent magnets 1134, 1136 are located in the same driver 1130 and are configured for placement on the same side of the body of the patient or subject. The motor 1132 may include, for example, a DC powered motor or servo that is powered via one or more batteries (not shown) integrally contained within the external adjustment device 1130. Alternatively, the motor 1132 may be powered via a power cord or the like to an external power source. For example, the external power source may include one or more batteries or even an alternating current source that is converted to DC.

Still referring to FIG. 10, the two permanent magnets 1134, 1136 are preferably cylindrically-shaped permanent magnets. The permanent magnets may be made from, for example, a rare earth magnet material such as Neodymium-Iron-Boron (NdFeB) although other rare earth magnets are also possible. For example, each magnet 1134, 1136 may have a length of around 1.5 inches and a diameter of around 1.0 to 3.5 inches. Both magnets 1134, 1136 are diametrically magnetized (poles are perpendicular the longitudinal axis of each permanent magnet 1134, 1136). The magnets 1134, 1136 may be contained within a non-magnetic cover or housing 1137. In this regard, the magnets 1134, 1136 are able to rotate within the stationary housing 1137 that separates the magnets 1134, 1136 from the external environment. Preferably, the housing 1137 is rigid and relatively thin walled at least at the portion directly covering the permanent magnets 1134, 1136, in order to minimize the gap between the permanent magnets 1134, 1136 and the magnetic assembly 236 (as shown in FIGS. 13A-13D).

As seen in FIG. 10, the permanent magnets 1134, 1136 are rotationally mounted between opposing bases members 1138, 1140. Each magnet 1134, 1136 may include axles or spindles 1142, 1144 mounted on opposing axial faces of each magnet 1134, 1136. The axles 1142, 1144 may be mounted in respective bearings (not shown) that are mounted in the base members 1138, 1140. As seen in FIG. 10, driven pulleys 1150 are mounted on one set of axles 1142 and 1144. The driven pulleys 1150 may optionally include grooves or teeth 1152 that are used to engage with corresponding grooves or teeth 1156 (partially illustrated in FIG. 11) contained within a drive belt (indicated by path 1154).

Figure 12:
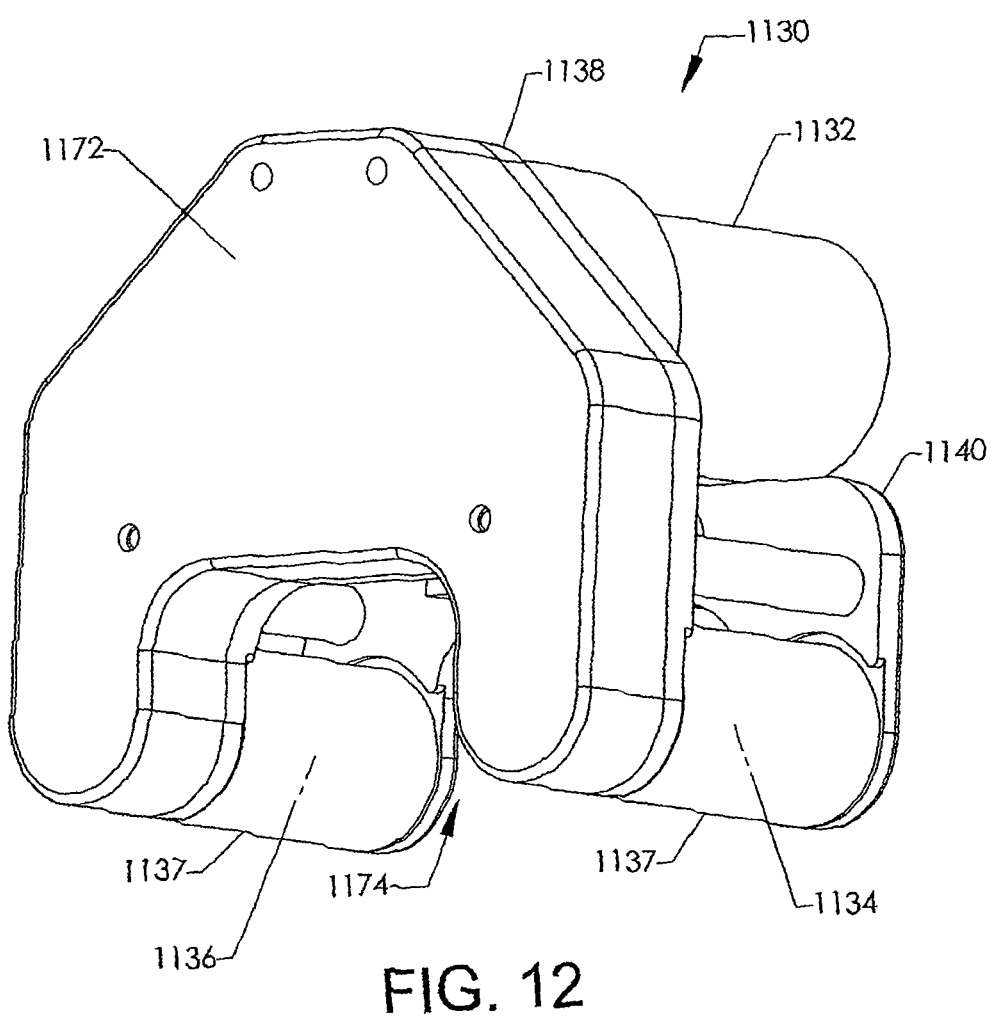
FIG. 12 illustrates a perspective view of an external adjustment device of FIG. 10 with the outer housing or cover in place.

Still referring to FIG. 10, the external adjustment device 1130 includes a drive transmission 1160 that includes the two driven pulleys 1150 along with a plurality of pulleys 1162A, 1162B, 1162C and rollers 1164A, 1164B, 1164C on which the drive belt 1154 is mounted. The pulleys 1162A, 1162B, 1162C may optionally include grooves or teeth 1166 used for gripping corresponding grooves or teeth 1156 of the drive belt 1154. Pulleys 1162A, 1162B, 1162C and rollers 1164A, 1164B, 1164C may be mounted on respective bearings (not shown). As seen in FIG. 10, pulley 1162B is mechanically coupled to the drive shaft (not shown) of the motor 1132. The pulley 1162B may be mounted directly to the drive shaft or, alternatively, may be coupled through appropriate gearing. One roller 1164B is mounted on a biased arm 1170 and thus provides tension to the belt 1154. The various pulleys 1150, 1162A, 1162B, 1162C and rollers 1164A, 1164B, 1164C along with the drive belt 1154 may be contained within a cover or housing 1172 that is mounted to the base 1138 (as seen in FIG. 12). For safety and convenience, it may be desired for the external adjustment device 1130 to have a removable safety cover that would be placed over the portion containing the permanent magnets 1134, 1136, for example during storage, so that the high magnetic field cannot come closely in contact with anything that would be strongly attracted to it or damaged by it. The external adjustment device 1130 may also be supplied in a case, for example, a case that has a sheet made of a magnetic shielding material, to minimize the magnetic field external to the case. Giron or mu-metal are two examples of this material.

Figure 11:
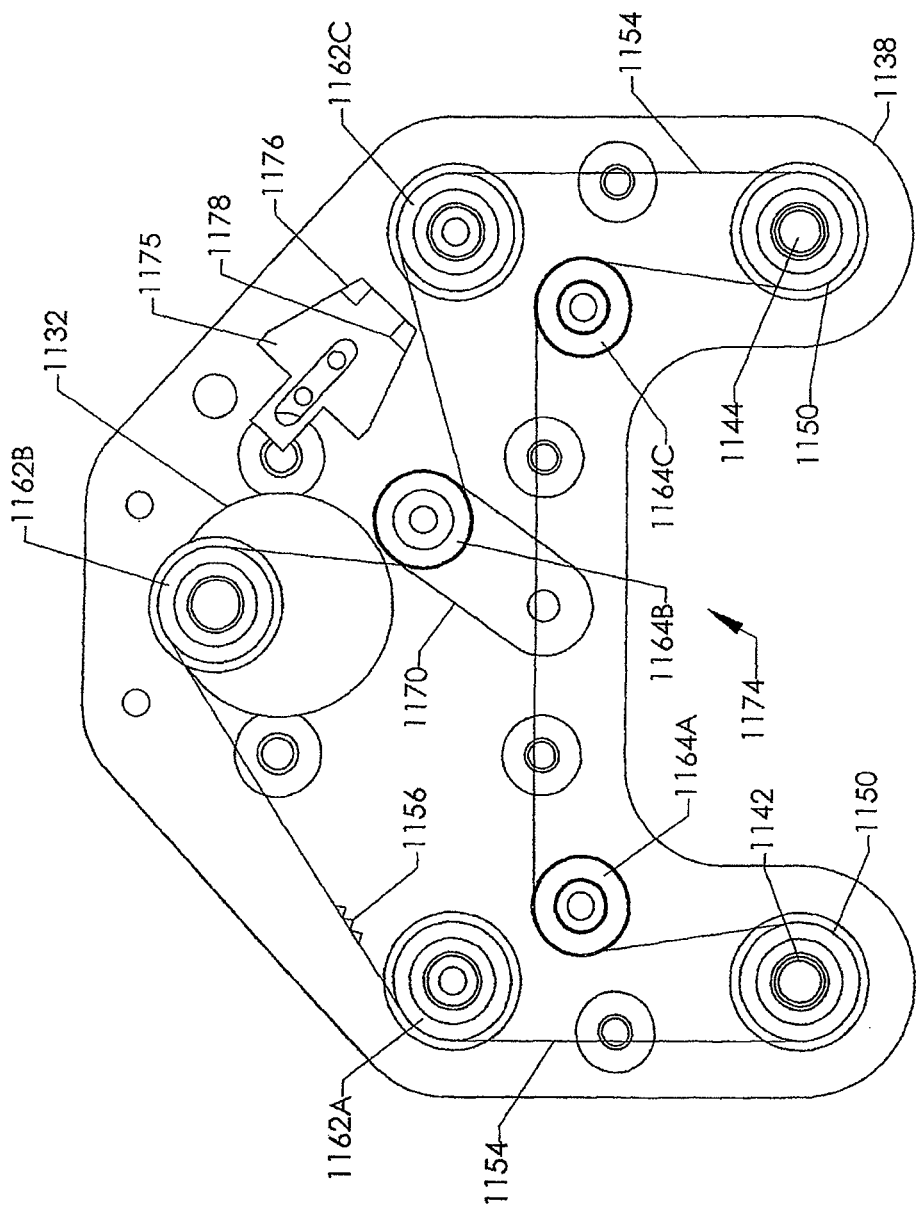
FIG. 11 illustrates a side or end view of the external adjustment device of FIG. 10.

As seen in FIGS. 10 and 11, rotational movement of the pulley 1162B causes the drive belt 1154 to move around the various pulleys 1150, 1162A, 1162B, 1162C and rollers 1164A, 1164B, 1164C. In this regard, rotational movement of the motor 1132 is translated into rotational movement of the two permanent magnets 1134, 1136 via the drive transmission 1160. In one aspect of the invention, the base members 1138, 1140 are cut so as to form a recess 1174 that is located between the two magnets 1134, 1136. During use, the external adjustment device 1130 is pressed against the skin of a patient, or against the clothing which covers the skin (e.g., the external adjustment device 1130 may be used through clothing so the patient may not need to undress). A small permanent magnet may be placed on the patient's clothing to determine the location of the implanted permanent magnet 254 (via the attraction of the two magnets). The recess 1174 allows skin as well as the underlying tissue to gather or compress within the recessed region 1174 as seen in FIGS. 13A and 13B. This advantageously reduces the overall distance between the external drive magnets 1134, 1136 and the permanent magnet 254 contained within the magnetic assembly 236 of the distraction device 200. By reducing the distance, this means that the externally located magnets 1134, 1136 and/or the internal magnet 1064 may be made smaller. This is especially useful in the case of an obese patient.

In one embodiment, the two permanent magnets 1134, 1136 are configured to rotate at the same angular velocity. In another embodiment, the two permanent magnets 1134, 1136 each have at least one north pole and at least one south pole, and the external adjustment device 1130 is configured to rotate the first magnet 1134 and the second magnet 1136 such that the angular location of the at least one north pole of the first magnet 1134 is substantially equal to the angular location of the at least one south pole of the second magnet 1136 through a full rotation of the first and second magnets 1134, 1136.

FIGS. 13A and 13B illustrate cross-sectional views of the patient having an implanted distraction device (not shown for sake of clarity) with a permanent magnet 254 contained within a magnetic assembly 236 (not shown in FIGS. 13A and 13B for clarity sake). The internal permanent magnet 254 is seen disposed on one side of a vertebra 1185. Further, the internal permanent magnet 254 is seen being outside or external with respect to the fascia 1184 and muscle 1186 of the subject. FIGS. 13A and 13B illustrate an obese patient in which skin and other tissue gather within the recess 1174. It should be understood that obese Adolescent Idiopathic Scoliosis patients are rare, and FIGS. 13A and 13B generally indicate a worst-case situation but as seen in FIGS. 13A and 13B the excess skin and other tissue are easily accommodated within the recess 1174 to enable close positioning between the internal permanent magnet 254 and the external drive magnets 1134, 1136. For most AIS patients, the air gap or distance between the internal permanent magnet 254 and the external drive magnets 1134, 1136 is generally one inch or less. In FIGS. 13A through 13D, the internal permanent magnet 254 is depicted somewhat larger than its actual size in order for its respective poles to be more clearly visible.

Still referring to FIGS. 10 and 11, the external adjustment device 1130 preferably includes an encoder 1175 that is used to accurately and precisely measure the degree of movement (e.g., rotational) of the external magnets 1134, 1136. In one embodiment, an encoder 1175 is mounted on the base member 1138 and includes a light source 1176 and a light receiver 1178. The light source 1176 may include a LED which is pointed or directed toward pulley 1162C. Similarly, the light receiver 1178 may be directed toward the pulley 1162C. The pulley 1162C includes a number of reflective markers 1177 regularly spaced about the periphery of the pulley 1162C. Depending on the rotational orientation of the pulley 1162C, light is either reflected or not reflected back onto the light receiver 1178. The digital on/off signal generated by the light receiver 1178 can then be used to determine the rotational speed and displacement of the external magnets 1134, 1136.

FIGS. 13A, 13B, 13C, and 13D illustrate the progression of the external magnets 1134, 1136 and the internal permanent magnet 254 that is located within the distraction device 200 during use. FIGS. 13A, 13B, 13C, and 13D illustrate the external adjustment device 1130 being disposed against the external surface of the patient's skin 1180 adjacent the spine. In the non-invasive adjustment procedure depicted, the patient 100 lies in a prone position, and the external adjustment device 1130 is placed upon the patient's back. However, the adjustment is conceived possible with the patient in supine, standing or positions. The external adjustment device 1130 is placed against the skin 1180 in this manner to remotely rotate the internal permanent magnet 254. As explained herein, rotation of the internal permanent magnet 254 causes rotational movement of the magnetic assembly 236. This rotational movement is then translated to the lead screw 260 via the locking pin 238 that connects the lead screw 260 to the magnetic assembly 236. Depending on the rotational direction of the lead screw 260, the distraction rod 206 moves in a telescopic manner out of or into the adjustable portion 208. In this regard, by controlling the rotational movement of the magnetic assembly 236 using the external adjustment device 1130, the operator is able to adjust the linear motion of the distraction rod 206 in a controllable manner. The magnetic assembly 236 may have rotational movement though less than 360° of a full rotation of the magnetic assembly 236. Alternatively, the magnetic assembly 236 may have rotational movement through more than 360° (e.g., multiple, full revolutions).

As seen in FIGS. 13A, 13B, 13C, and 13D, the external adjustment device 1130 may be pressed down on the patient's skin 1180 with some degree of force such that skin 1180 and other tissue such as the underlying layer of fat 1182 are pressed or forced into the recess 1174 of the external adjustment device 1130. FIGS. 13A, 13B, 13C, and 13D show the magnetic orientation of the internal permanent magnet 254 as it undergoes a full rotation in response to movement of the permanent magnets 1134, 1136 of the external adjustment device 1130.

With reference to FIG. 13A, the internal permanent magnet 254 is shown being oriented with respect to the two permanent magnets 1134, 1136 via an angle θ. This angle θ may depend on a number of factors including, for instance, the separation distance between the two permanent magnets 1134, 1136, the location or depth of where the implantable interface 1104 is located, the degree of force at which the external adjustment device 1130 is pushed against the patient's skin. Generally in applications including some obese patients, the angle θ should be at or around 90° to achieve maximum drivability (e.g., torque). The inventors have calculated that in the AIS application, where there are few obese patients, an angle of about 70° is preferred for the majority of patients when the permanent magnets 1134, 1136 have an outer diameter of about two (2.0) to three (3.0) inches.

FIG. 13A illustrates the initial position of the two permanent magnets 1134, 1136 and the internal permanent magnet 254. This represents the initial or starting location (e.g., 0° position as indicated). Of course, it should be understood that, during actual use, the particular orientation of the two permanent magnets 1134, 1136 and the internal permanent magnet 254 will vary and not likely will have the starting orientation as illustrated in FIG. 13A. In the starting location illustrated in FIG. 13A, the two permanent magnets 1134, 1136 are oriented with their poles in an N-S/S-N arrangement. The internal permanent magnet 254 is, however, oriented generally perpendicular to the poles of the two permanent magnets 1134, 1136.

FIG. 13B illustrates the orientation of the two permanent magnets 1134, 1136 and the internal permanent magnet 254 after the two permanent magnets 1134, 1136 have rotated through 90°. The two permanent magnets 1134, 1136 rotate in the direction of arrow A (e.g., clockwise) while the internal permanent magnet 254 rotates in the opposite direction (e.g., counter clockwise) represented by arrow B. It should be understood that the two permanent magnets 1134, 1136 may rotate in the counter clockwise direction while the internal permanent magnet 254 may rotate in the clockwise direction. Rotation of the two permanent magnets 1134, 1136 and the internal permanent magnet 254 continues as represented by the 180° and 270° orientations as illustrated in FIGS. 13C and 13D. Rotation continues until the starting position) (0° is reached again.

During operation of the external adjustment device 1130, the permanent magnets 1134, 1136 may be driven to rotate the internal permanent magnet 254 through one or more full rotations in either direction to increase or decrease distraction of the distraction device 200 as needed. Of course, the permanent magnets 1134, 1136 may be driven to rotate the internal permanent magnet 254 through a partial rotation as well (e.g., ¼, ⅛, ¹⁄₁₆, etc.). The use of two magnets 1134, 1136 is preferred over a single external magnet because the internal permanent magnet 254 may not be oriented perfectly at the start of rotation, so one external magnet 1134, 1136 may not be able to deliver its maximum torque, which depends on the orientation of the internal permanent magnet 254 to some degree. However, when two (2) external magnets (1134, 1136) are used, one of the two 1134 or 1136 will have an orientation relative to the internal permanent magnet 254 that is better or more optimal than the other. In addition, the torques imparted by each external magnet 1134, 1136 are additive. In prior art magnetically driven devices, the external driving device is at the mercy of the particular orientation of the internal driven magnet. The two-magnet embodiment described herein is able to guarantee a larger driving torque—as much as 75% more than a one-magnet embodiment in the AIS application—and thus the internal permanent magnet 254 can be designed smaller in dimension, and less massive. A smaller internal permanent magnet 254 will have a smaller image artifact when performing MRI (Magnetic Resonance Imaging), especially important when using pulse sequences such as gradient echo, which is commonly used in breast imaging, and leads to the largest artifact from implanted magnets. In certain configurations, it may even be optimal to use three or more external magnets, including one or more magnets each on two different sides of the body (for example front and back).

Figure 14:
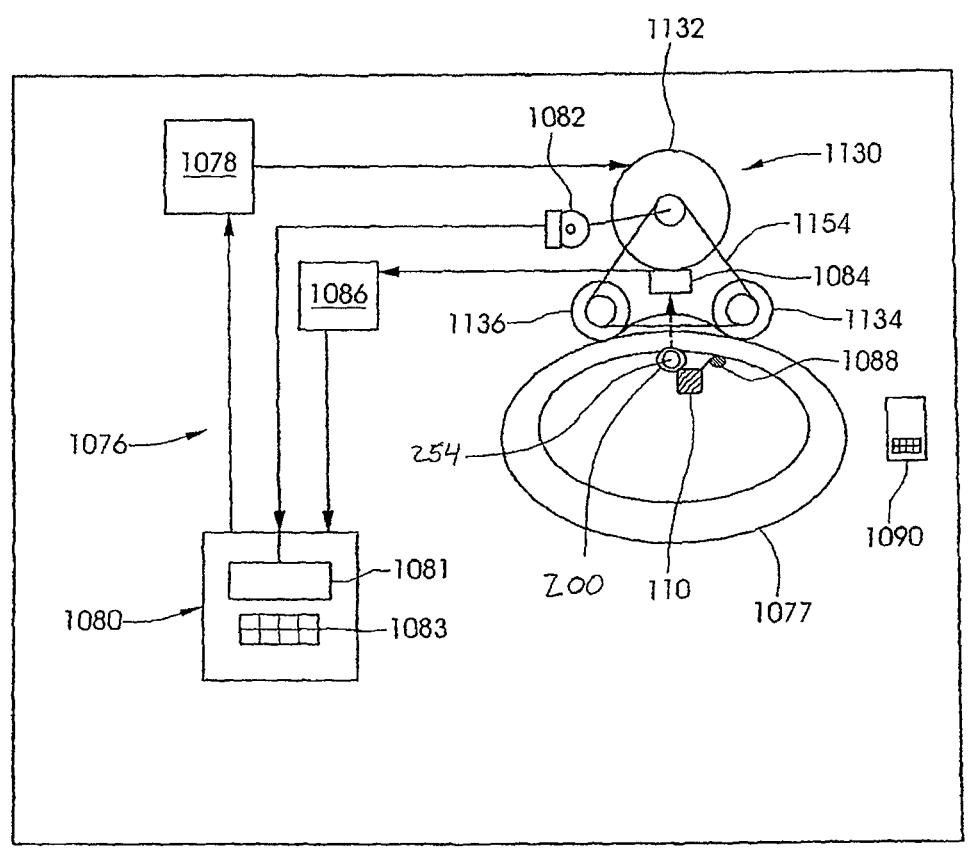
FIG. 14 schematically illustrates a system for driving the external adjustment device according to one embodiment.

FIG. 14 illustrates a system 1076 according to one aspect of the invention for driving the external adjustment device 1130. FIG. 14 illustrates the external adjustment device 1130 pressed against the surface of a patient 1077 (torso face down shown in cross-section). The portion of the distraction device 200 containing the internal permanent magnet 254 is illustrated. The permanent magnet 254 that is located within the magnetic assembly 236 (disposed internally within the patient 1077 is magnetically coupled through the patient's skin and other tissue to the two external magnets 1134, 1136 located in the external adjustment device 1130. As explained herein, one rotation of the external magnets 1134, 1136 causes a corresponding single rotation of the magnetic assembly 236 (which contains the permanent magnet 254). Turning magnetic assembly 236 in one direction causes the distraction device 200 to lengthen, or increase distraction force while turning in the opposite direction causes the distraction device 200 to shorten, or decrease distraction force. Changes to the distraction device 200 are directly related to the number of turns of the magnetic assembly 236.

The motor 1132 of the external adjustment device 1130 is controlled via a motor control circuit 1078 operatively connected to a programmable logic controller (PLC) 1080. The PLC 1080 outputs an analog signal to the motor control circuit 1078 that is proportional to the desired speed of the motor 1132. The PLC 1080 may also select the rotational direction of the motor 1132 (i.e., forward or reverse). In one aspect, the PLC 1080 receives an input signal from a shaft encoder 1082 that is used to identify with high precision and accuracy the exact relative position of the external magnets 1134, 1136. For example, the shaft encoder 1082 may be an encoder 1175 as described in FIGS. 10-11. In one embodiment, the signal is a pulsed, two channel quadrature signal that represents the angular position of the external magnets 1134, 1136. The PLC 1080 may include a built in screen or display 1081 that can display messages, warnings, and the like. The PLC 1080 may optionally include a keyboard 1083 or other input device for entering data. The PLC 1080 may be incorporated directly into the external adjustment device 1130 or it may be a separate component that is electrically connected to the main external adjustment device 1130.

In one aspect of the invention, a sensor 1084 is incorporated into the external adjustment device 1130 that is able to sense or determine the rotational or angular position of the internal permanent magnet 254. The sensor 1084 may acquire positional information using, for example, sound waves, ultrasonic waves, light, radiation, or even changes or perturbations in the magnetic or electromagnetic field between the internal permanent magnet 254 and the external magnets 1134, 1136. For example, the sensor 1084 may detect photons or light that is reflected from the internal permanent magnet 254 or a coupled structure (e.g., rotor) that is attached thereto. For example, light may be passed through the patient's skin and other tissue at wavelength(s) conducive for passage through tissue. Portions of the internal permanent magnet 254 or associated structure may include a reflective surface that reflects light back outside the patient as the internal permanent magnet 254 moves. The reflected light can then be detected by the sensor 1084 which may include, for example, a photodetector or the like.

In another aspect, the sensor 1084 may operate on the Hall effect, wherein two additional magnets are located within the implantable assembly. The additional magnets move axially in relation to each other as the internal permanent magnet 254 rotates and therefore as the distraction increases or decreases, allowing the determination of the current size of the restriction device.

In the embodiment of FIG. 14, the sensor 1084 is a microphone disposed on the external adjustment device 1130. For instance, the microphone sensor 1084 may be disposed in the recessed portion 1174 of the external adjustment device 1130. The output of the microphone sensor 1084 is directed to a signal processing circuit 1086 that amplifies and filters the detected acoustic signal. In this regard, the acoustic signal may include a "click" or other noise that is periodically generated by rotation of the internal permanent magnet 254. For example, the internal permanent magnet 254 may click every time a full rotation is made. The pitch (frequency) of the click may differ depending on the direction of rotation. For example, rotation in one direction (e.g., lengthening) may produce a low pitch while rotation in the other direction (e.g., shortening) may produce a higher pitch signal (or vice versa). The amplified and filtered signal from the signal processing circuit 1086 can then pass to the PLC 1080. Additional details regarding the operation of various acoustic and other detection modalities may be found in U.S. patent application Ser. No. 12/121,355.

During operation of the system 1076, each patient will have a number or indicia that correspond to the adjustment setting or size of their distraction device 200. This number can be stored on an optional storage device 1088 (as shown in FIG. 14) that is carried by the patient (e.g., memory card, magnetic card, or the like) or is integrally formed with the distraction device 200. For example, a RFID tag 1088 implanted either as part of the system or separately may be disposed inside the patient (e.g., subcutaneously or as part of the device) and can be read and written via an antenna 1090 to update the current size of the distraction device 200. In one aspect, the PLC 1080 has the ability to read the current number corresponding to the size or setting of the distraction device 200 from the storage device 1088. The PLC 1080 may also be able to write the adjusted or more updated current size or setting of the distraction device 200 to the storage device 1088. Of course, the current size may recorded manually in the patient's medical records (e.g., chart, card or electronic patient record) that is then viewed and altered, as appropriate, each time the patient visits his or her physician.

The patient, therefore, carries their medical record with them, and if, for example, they are in another location, or even country, and need to be adjusted, the RFID tag 1088 has all of the information needed. Additionally, the RFID tag 1088 may be used as a security device. For example, the RFID tag 1088 may be used to allow only physicians to adjust the distraction device 200 and not patients. Alternatively, the RFID tag 1088 may be used to allow only certain models or makes of distraction devices to be adjusted by a specific model or serial number of external adjustment device 1130.

In one aspect, the current size or setting of the distraction device 200 is input into the PLC 1080. This may be done automatically or through manual input via, for instance, the keyboard 1083 that is associated with the PLC 1080. The PLC 1080 thus knows the patient's starting point. If the patient's records are lost, the length of the distraction device may be measured by X-ray and the PLC 1080 may be manually programmed to this known starting point.

The external adjustment device 1130 is commanded to make an adjustment. This may be accomplished via a pre-set command entered into the PLC 1080 (e.g. "increase distraction displacement of distraction device 200 by 0.5 cm" or "increase distraction force of distraction device 200 to 20 pounds"). The PLC 1080 configures the proper direction for the motor 1132 and starts rotation of the motor 1132. As the motor 1132 spins, the encoder 1082 is able to continuously monitor the shaft position of the motor directly, as is shown in FIG. 14, or through another shaft or surface that is mechanically coupled to the motor 1132. For example, the encoder 1082 may read the position of markings 1177 located on the exterior of a pulley 1162C like that disclosed in FIG. 10. Every rotation or partial rotation of the motor 1132 can then be counted and used to calculate the adjusted or new size or setting of the distraction device 200.

The sensor 1084, which may include a microphone sensor 1084, may be monitored continuously. For example, every rotation of the motor 1132 should generate the appropriate number and pitch of clicks generated by rotation of the permanent magnet inside the distraction device 200. If the motor 1132 turns a full revolution but no clicks are sensed, the magnetic coupling may have been lost and an error message may be displayed to the operator on a display 1081 of the PLC 1080. Similarly, an error message may be displayed on the display 1081 if the sensor 1084 acquires the wrong pitch of the auditory signal (e.g., the sensor 1084 detects a shortening pitch but the external adjustment device 1130 was configured to lengthen).

While embodiments of the present invention have been shown and described, various modifications may be made without departing from the scope of the present invention. The invention, therefore, should not be limited, except to the following claims, and their equivalents.

What is claimed is:

1. A spinal distraction system comprising:
    a distraction rod having a first end configured for affixation to a subject's spine at a first location and a second end containing a recess having a threaded portion disposed therein; and
    an adjustable portion configured for affixation to the subject's spine at a second location remote from the first location, the adjustable portion comprising:
    a lead screw,
    a housing extending along a longitudinal axis, the housing containing a permanent magnet and the lead screw, wherein the housing contains the permanent magnet in close proximity to a first end of the housing, and wherein the permanent magnet is configured to rotate the lead screw about the longitudinal axis within the housing, the lead screw being operatively coupled to the threaded portion of the distraction rod, and wherein the housing further includes an open end at a second end that is opposite the first end, and
    a locking pin passing transversely through the lead screw configured to couple the permanent magnet to the lead screw to permit angular displacement of the lead screw relative to the magnet within the housing,
    wherein upon rotating the lead screw by the permanent magnet, the lead screw is configured to communicate with the threaded portion of the distraction rod to telescopically move the distraction rod into and out of the open end of the housing of the adjustable portion and change an axial length of the spinal distraction system.

2. The spinal distraction system of claim 1, wherein the locking pin comprises heat treated stainless steel.

3. The spinal distraction system of claim 1, comprising a magnet assembly having a first cup and a second cup with the permanent magnet located in a recess formed between the first cup and the second cup.

4. The spinal distraction system of claim 3, the first cup comprising a receptacle having an aperture dimensioned to receive the locking pin.

5. The spinal distraction system of claim 4, further comprising a bearing disposed within the housing of the adjustable portion.

6. The spinal distraction system of claim 4, wherein the receptacle is dimensioned to permit angular displacement of the lead screw relative to a longitudinal axis of the magnetic assembly.

7. The spinal distraction system of claim 1, comprising at least one O-ring dimensioned to form a fluid tight seal between the housing and the distraction rod.

8. The spinal distraction system of claim 7, wherein the at least one O-ring has a compression value that ranges from 13% to 18%.

9. The spinal distraction system of claim 7, wherein the at least one O-ring is coated with a lubricant.

10. The spinal distraction system of claim 7, wherein the fluid tight seal comprises an air tight seal.

11. The spinal distraction system of claim 10, wherein an interior between the housing and the distraction rod has a positive air pressure configured to permit movement of the distraction rod while sealing the interior of the housing.

12. The spinal distraction system of claim 7, further comprising an external adjustment device and wherein the lead screw is configured to rotate in a first direction to increase the axial length of the spinal distraction system and configured to rotate in a second opposite direction to decrease the axial length of the spinal distraction system.

13. The spinal distraction system of claim 1, the housing comprising a stop in close proximity to the open end, and the distraction rod comprising a splined tip, the stop of the housing configured to prevent the splined tip of the distraction rod from exiting the housing, and thereby maintaining the distraction rod with respect to the housing.

14. The spinal distraction system of claim 1, wherein the permanent magnet comprises a cylindrical magnet.

15. The spinal distraction system of claim 1, the threaded portion bonded to the distraction rod by an adhesive material.

16. The spinal distraction system of claim 15, the threaded portion comprising a material that is different from the material of the lead screw.

17. The spinal distraction system of claim 16, the threaded portion comprising a softer material than the material of the lead screw.

18. The spinal distraction system of claim 17, the lead screw comprising titanium.

19. The spinal distraction system of claim 17, the lead screw comprising aluminum bronze.

* * * * *